United States Patent
Hoelke et al.

(12) 
(10) Patent No.: US 6,406,899 B1
(45) Date of Patent: Jun. 18, 2002

(54) HIGHLY ACTIVE ALKALINE PHOSPHATASE

(75) Inventors: Werner Hoelke; Rainer Muller, both of Penzberg; Helmut Burtscher, Habach, all of (DE); Jose Luis Millan, San Diego, CA (US)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/305,681

(22) Filed: May 5, 1999

(30) Foreign Application Priority Data

May 5, 1998 (DE) ......................... 198 19 962

(51) Int. Cl.$^7$ ........................... C12N 9/16; C12N 1/20; C12N 15/00; C07H 21/04; C07K 1/00
(52) U.S. Cl. ................. 435/196; 435/252.3; 435/320.1; 536/23.2; 530/350
(58) Field of Search .............................. 435/196, 252.3, 435/320.1; 536/23.2; 530/350

(56) References Cited

U.S. PATENT DOCUMENTS

| | | | |
|---|---|---|---|
| 5,707,853 A | 1/1998 | Millan | 435/252.3 |
| 5,773,226 A | * | 6/1998 | Millan | 435/7.9 |

FOREIGN PATENT DOCUMENTS

| | | |
|---|---|---|
| EP | 0151320 A2 | 8/1985 |
| EP | 0 584 343 B1 | 1/1999 |

OTHER PUBLICATIONS

Sequence alignment of Applicants' SEQ ID NO : 2, 4, and 6.*

Besman, Marc et al., "Isozymes of Bovine Intestinal Alkaline Phospatase", The Journal of Biological Chemistry, vol. 260, No. 20, Issue of Sep. 15, 1985, pp. 11190–11193.

Grotelueschen, Jeff, et al., "Cloning and Characterization of the pho–2+ Gene Encoding a Repressible Alkaline Phosphatase in Neurospora Crassa", Gene, 144 (1994) 147–148, 1994 Elsevier Science B.V., Gene 07956.

Manes, Thomas, et al., "Genetic Complexity, Structure, and Characterization of Highly Active Bovine Intestinal Alkaline Phosphatases", The Journal of Biological Chemistr, 1998 by the American Society for Biochemistry and Molecular Biology, Inc., vol. 273, No. 36, Issue of Sep. 4, pp. 23353–23360.

"Calf Intestine Alkaline Phosphatases" Calzyme Laboratories Online Catalog, CAT, Nos. 235B4500 and 140B4500, 1997, XP002184761.

DATABASE WPI, Week 199445, Derwent Publications Ltd., London, GB; AN 1994–362592, XP002153653, "Recombinant Human Enteric Alkaline Phosphatase", (TOSOH CORP.).

* cited by examiner

*Primary Examiner*—Ponnathapu Achutamurthy
*Assistant Examiner*—Tekchand Saidha
(74) *Attorney, Agent, or Firm*—Kenneth J. Waite; Roche Diagnostics Corporation

(57) ABSTRACT

The invention concerns a DNA coding a eukaryotic highly active alkaline phosphatase with a specific activity of more than 3000 U/mg. The invention also concerns a process for the production of a DNA according to the invention, a vector containing the DNA according to the invention and a cell line containing this vector. Furthermore the invention concerns a recombinant highly active alkaline phosphatase with a specific activity of more than 3000 U/mg which is coded by the DNA according to the invention.

10 Claims, 13 Drawing Sheets

Figure 1/1

```
   1 GAATTCGGCA CGAGCCAGGT CCCATCCTGA CCCTCCGCCA TCACACAGCT
  51 ATGCAGTGGG CCTGTGTGCT GCTGCTGCTG GGCCTGTGGC TACAGCTCTC
 101 CCTCACCCTC ATCCCAGCTG AGGAGGAAAA CCCCGCCTTC TGGAACCGCC
 151 AGGCAGCCCA GGCCCTTGAT GTAGCCAAGA AGTTGCAGCC GATCCAGACA
 201 GCTGCCAAGA ATGTCATCCT CTTCTTGGGG GATGGGATGG GGTGCCTAC
 251 GGTGACAGCC ACTCGGATCC TAAAGGGGCA GATGAATGGC AAACTGGGAC
 301 CTGAGACACC CCTGGCCATG GACCAGTTCC CATACGTGGC TCTGTCCAAG
 351 ACATACAACG TGGACAGACA GGTGCCAGAC AGCGCAGGCA CTGCCACTGC
 401 CTACCTGTGT GGGGTCAAGG GCAACTACAG AACCATCGGT GTAAGTGCAG
 451 CCGCCCGCTA CAATCAGTGC AACACGACAC GTGGGAATGA GGTCACGTCT
 501 GTGATCAACC GGGCCAAGAA AGCAGGGAAG GCCGTGGGAG TGGTGACCAC
 551 CACCAGGGTG CAGCATGCCT CCCCAGCCGG GGCCTACGCG CACACGGTGA
 601 ACCGAAACTG GTACTCAGAC GCCGACCTGC CTGCTGATGC ACAGAAGAAT
 651 GGCTGCCAGG ACATCGCCGC ACAGCTGGTC TACAACATGG ATATTGACGT
 701 GATCCTGGGT GGAGGCCGAA TGTACATGTT CCCTGAGGGG ACCCCAGACC
 751 CTGAATACCC AGATGATGCC AGTGTGAATG GAGTCCGGAA GGACAAGCAG
 801 AACCTGGTGC AGGAATGGCA GGCCAAGCAC CAGGGAGCCC AGTATGTGTG
 851 GAACCGCACT GCGCTCCTTC AGGCGGCCGA TGACTCCAGT GTAACACACC
 901 TCATGGGCCT CTTTGAGCCG GCAGACATGA AGTATAATGT TCAGCAAGAC
 951 CACACCAAGG ACCCGACCCT GGCGGAGATG ACGGAGGCGG CCCTGCAAGT
1001 GCTGAGCAGG AACCCCCGGG GCTTCTACCT CTTCGTGGAG GGAGGCCGCA
1051 TTGACCACGG TCACCATGAC GGCAAAGCTT ATATGGCACT GACTGAGGCG
1101 ATCATGTTTG ACAATGCCAT CGCCAAGGCT AACGAGCTCA CTAGCGAACT
1151 GGACACGCTG ATCCTTGTCA CTGCAGACCA CTCCCATGTC TTCTCTTTTG
1201 GTGGCTACAC ACTGCGTGGG ACCTCCATTT TCGGTCTGGC CCCCGGCAAG
```

Figure 1/2

```
1251    GCCTTAGACA  GCAAGTCCTA  CACCTCCATC  CTCTATGGCA  ATGGCCCAGG
1301    CTATGCGCTT  GGCGGGGGCT  CGAGGCCCGA  TGTTAATGGC  AGCACAAGCG
1351    AGGAACCCTC  ATACCGGCAG  CAGGCGGCCG  TGCCCCTGGC  TAGCGAGACC
1401    CACGGGGGCG  AAGACGTGGC  GGTGTTCGCG  CGAGGCCCGC  AGGCGCACCT
1451    GGTGCACGGC  GTGCAGGAGG  AGACCTTCGT  GGCGCACATC  ATGGCCTTTG
1501    CGGGCTGCGT  GGAGCCCTAC  ACCGACTGCA  ATCTGCCAGC  CCCCGCCACC
1551    GCCACCAGCA  TCCCCGACGC  CGCGCACCTG  GCGGCCAGCC  CGCCTCCACT
1601    GGCGCTGCTG  GCTGGGGCGA  TGCTGCTGCT  GCTGGCGCCC  ACCTTGTACT
1651    AACCCCCACC  AGTTCCAGGT  CTCGGGATTT  CCCGCTCTCC  TGCCCAAAAC
1701    CTCCCAGCTC  AGGCCCTACC  GGAGCTACCA  CCTCAGAGTC  CCCACCCCGA
1751    AGTGCTATCC  TAGCTGCCAC  TCCTGCAGAC  CCGACCCAGC  CGGAATTC
```

Figure 2

```
        10        20        30        40        50        60        70        80
LIPAEEENPAFWNRQAAQALDVAKKLQPIQTAAKNVILFLGDGMGVPTVTATRILKGQMNGKLGPETPLAMDQFPYVALS 90       100       110       120   130       140       150       160
KTYNVDRQVPDSAGTATAYLCGVKGNYRTIGVSAAARYNQCNTTRGNEVTSVINRAKKAGKAVGVVTTTRVQHASPAGAY
                                                             M 170       180       190       200       210       220       230       240
AHTVNRNWYSDADLPADAQKNGCQDIAAQLVYNMDIDVILGGGRMYMFPEGTPDPEYPDDASVNGVRKDKQNLVQEWQAK
                                              K 250       260       270       280       290       300       310       320
HQGAQYVWNRTALLQAADDSSVTHLMGLFEPADMKYNVQQDHTKDPTLAEMTEAALQVLSRNPRGFYLFVEGGRIDHGHH
          MK 330       340       350       360       370       380       390       400
DGKAYMALTEAIMFDNAIAKANELTSELDTLILVTADHSHVFSFGGYTLRGTSIFGLAPGKALDSKSYTSILYGNGPGYA
                                                    S
                                                         S 410       420       430       440       450       460       470       480
LGGGSRPDVNGSTSEEPSYRQQAAVPLASETHGGEDVAVFARGPQAHLVHGVQEETFVAHIMAFAGCVEPYTDCNLPAPA
                                                                               T
```

............. Direct N-terminal sequence
─────────── Cleavage with endoproteinase LysC
─ ─ ─ ─ ─ ─ Cleavage with trypsin
─ · ─ · ─ · Cleavage with cyanogen bromide
· · · · · · Cleavage with endoproteinase AspN
─ · · ─ · · Cleavage with endoproteinase GluC
·········· Carboxypeptidase digest
○ Carbohydrate

Figure 3/1

```
   1  GAATTCGGCA CGAGCGAGAC CCAGACTCCC CAGGTCCCAT CCTGACCCTC
  51  CGCCATCACA CAGCTATGCA GGGGGCCTGC GTGCTGCTGC TGCTGGGCCT
 101  GTGGCTACAG CTCTCCCTCG CCTTCATCCC AGTTGAGGAG GAAGACCCCG
 151  CCTTCTGGAA CCGCCAGGCA GCCCAGGCCC TTGATGTGGC TAAGAAGCTG
 201  CAGCCCATCC AGAAAGCCGC CAAGAATGTC ATCCTCTTCT GGGAGATGG
 251  GATGGGGGTG CCTACGGTGA CAGCCACTCG GATACTGAAG GGGCAGATGA
 301  ATGACAAGCT GGGACCTGAG ACACCCTGG CCATGGACCA GTTCCCATAC
 351  GTGGCTCTGT CCAAGACATA CAACGTGGAC AGACAGGTGC AGACAGCGC
 401  AGGCACTGCC ACTGCCTACC TGTGTGGGGT CAAGGGCAAC TACAGAACCA
 451  TCGGTGTAAG TGCAGCCGCC CGCTACAATC AGTGCAACAC GACACGTGGG
 501  AATGAGGTCA CGTCTGTGAT GAACCGGGCC AAGAAGCAG GGAAGTCAGT
 551  GGGAGTGGTG ACCACCACCA GGGTGCAGCA CGCCTCCCA GCCGGTGCTT
 601  ATGCACACAC GGTGAACCGT GACTGGTACT CAGACGCCGA CCTGCCTGCC
 651  GATGCACAGA CGTATGGCTG CCAGGACATC GCCACACAAC TGGTCAACAA
 701  CATGGATATT GACGTGATCC TGGGTGGAGG CCGAAAGTAC ATGTTTCCTG
 751  AGGGGACCCC AGACCCTGAA TACCCACACG ATGCCAGTGT GAATGGAGTC
 801  CGGAAGGACA GCGGAATCT GGTGCAGGAG TGGCAGGCCA AGCACCAGGG
 851  AGCCCAGTAT GTGTGGAACC GCACGGAGCT CCTTCAGGCA GCCAATGACT
 901  CCAGTGTTAC ACATCTCATG GGCCTCTTTG AGCCGGCAGA CATGAAGTAT
 951  AATGTTCAGC AAGACCCCAC CAAGGACCCG ACCCTGGAGG AGATGACGGA
1001  GGCGGCCCTG CAAGTGCTGA GCAGGAACCC CCAGGGCTTC TACCTCTTCG
1051  TGGAGGGAGG CCGCATTGAC CACGGTCACC ATGATAGCAA AGCTTATATG
1101  GCGCTGACTG AGGCGGTCAT GTTTGACAAT GCCATCGCCA AGGCTAACGA
1151  GCTCACTAGC GAACTGGACA CGCTGATCCT TGTCACTGCA GACCACTCCC
1201  ATGTCTTCTC TTTTGGTGGC TACACACTGC GTGGGACCTC CATTTTCGGT
```

Figure 3/2

```
1251  CTGGCCCCCA GCAAGGCCTC AGACAAGAAG TCCTACACCT CCATCCTCTA
1301  TGGCAATGGC CCTGGCTACG TGCTTGGTGG GGGCTCAAGG CCCGATGTTA
1351  ATGACAGCAT AAGCGAGGAC CCCTCATACC GGCAGCAGGC GGCCGTGCCC
1401  CTGTCTAGCG AGACCCACGG GGGCGAAGAC GTGGCGGTGT TCGCGCGAGG
1451  CCCGCAGGCG CACCTGGTGC ACGGCGTGCA GGAGGAGACC TTCGTGGCGC
1501  ACGTCATGGC CTTTGCGGGC TGCGTGGAGC CCTACACCGA CTGCAATCTG
1551  CCGGCCCCCT CTGGCCTCTC CGACGCCGCG CACCTGGCGG CCAGCGCGCC
1601  TTCGCTAGCG CTGCTGGCCG GGCGATGCT GCTGCTGCTG GCGCCCGCCT
1651  TGTACTGACC CCACCAACT CCAGGTCTTG GGTTTCCCG CTTTCTTGCC
1701  CCAAAATCTC CAGCGCAGG CCCCATCTGA GCTACCACCT CAGAGTCCCC
1751  ACCCTGAAGT CCTATCTAGC GCACTCCAGA CCGCGACTCA GCCCCACCAC
1801  CAGAGCTTCA CCTCCCAGCA ACGAAGGAGC CTTAGCTCAC AGCCTTTCAT
1851  GGCCCAGACC ATTCTGGAGA CTGAGGCCCT GATTTTCCCG ACCCAACTTC
1901  AGTGGCTTGA GATTTTGTGT TCTGCCACCC CGGATCCCTG TAAGGGGGCT
1951  CGGACCATCC AGACTCCCCC CACTGCCCAC AGCCGAACCT GAGGACCAGG
2001  CTGGCACGGT CCCAGGGGTC CCAGGCCCGG CTGGAACCCA CATCTTTGCC
2051  TTTCAGGAGA CCCTGGGACT GTGGGGTTTC CAGGAGGCGT GGCTTCTTGG
2101  AGGCGTGGCT TCGGAGGGGT GGCTTCCGAG AAGGCGTGGC TCCCTGTCCT
2151  GGAACCACCC TGTGGGNATC TGGGGCCCAA GGAGATGTCT GGGGCAAAGA
2201  GTGCCGGGGG ACCCTGGACA CAGAATCTTC AGCGGCCCCT CCTAGGAACC
2251  CAGCAGTACC ATTATAGAGA GGGGACACCG ACACAGAGGA GAGGAGACTT
2301  GTCCCAGGTC CCTCAGCTGC TGTGAGGGGT GACCCTTGGT TCCCGTTACC
2351  AGGCTGGGGG ATCCCAGGAG CAGCGGGGGA CCTGGGGGTG GGGACACAGG
2401  CCCCACACTC CTGGGAGGGA GGAAGCAGCC CTNAAATAAA CTGTTCCTCG
2451  TGCCGAATTC
```

Figure 4

```
  1  FIPVEEEDPA  FWNRQAAQAL  DVAKKLQPIQ  KAAKNVILFL  GDGMGVPTVT
 51  ATRILKGQMN  DKLGPETPLA  MDQFPYVALS  KTYNVDRQVP  DSAGTATAYL
101  CGVKGNYRTI  GVSAAARYNQ  CNTTRGNEVT  SVMNRAKKAG  KSVGVVTTTR
151  VQHASPAGAY  AHTVNRDWYS  DADLPADAQT  YGCQDIATQL  VNNMDIDVIL
201  GGGRKYMFPE  GTPDPEYPHD  ASVNGVRKDK  RNLVQEWQAK  HQGAQYVWNR
251  TELLQAANDS  SVTHLMGLFE  PADMKYNVQQ  DPTKDPTLEE  MTEAALQVLS
301  RNPQGFYLFV  EGGRIDHGHH  DSKAYMALTE  AVMFDNAIAK  ANELTSELDT
351  LILVTADHSH  VFSFGGYTLR  GTSIFGLAPS  KASDKKSYTS  ILYGNGPGYV
401  LGGGSRPDVN  DSISEDPSYR  QQAAVPLSSE  THGGEDVAVF  ARGPQAHLVH
451  GVQEETFVAH  VMAFAGCVEP  YTDCNLPAPS  GLSDAAHLAA  SAPSLALLAG
501  AMLLLLAPAL  Y
```

Figure 5/1

```
   1  GAATTCGGCA CGAGGAGACC CGGCCTCCCC AGGTCCCATC CTGACCCTCC
  51  GCCATCACAC AGCCATGCAG TGGGCCTGTG TGCTGCTGCT GCTGGGCCTG
 101  TGGCTACAGC TCTCCCTCAC CTTCATCCCA GCTGAGGAGG AAGACCCCGC
 151  CTTCTGGAAC CGCCAGGCAG CCCAGGCCCT TGATGTAGCC AAGAAGTTGC
 201  AGCCGATCCA GACAGCTGCC AAGAATGTCA TCCTCTTCTT GGGGGATGGG
 251  ATGGGGGTGC CTACGGTGAC AGCCACTCGG ATCCTAAAGG GGCAGATGAA
 301  TGGTAAGCTG GGACCTGAGA CACCCCTGGC CATGGACCAG TTCCCATACG
 351  TGGCTCTGTC AAGACATAC AACGTGGACA GACAGGTGCC AGACAGCGCA
 401  GGCACTGCCA CTGCCTACCT GTGTGGGGTC AAGGGCAACT ACAAAACCAT
 451  TGGTGTAAGT GCAGCCGCCC GCTACAACCA GTGCAACACA ACAAGTGGCA
 501  ATGAGGTCAC GTCTGTGATG AACCGGGCCA AGAAGCAGG AAAGTCAGTG
 551  GGAGTGGTGA CCACCTCCAG GGTGCAGCAT GCCTCCCAG CCGGTGCTTA
 601  TGCACACACG GTGAACCGAA ACTGGTACTC AGATGCCGAC TGCCTGCCG
 651  ATGCACAGAC GTATGGCTGC CAGGACATCG CCACACAACT GGTCAACAAC
 701  ATGGATATTG ACGTGATCCT GGGTGGAGGC CGAATGTACA TGTTTCCTGA
 751  GGGGACCCCG GATCCTGAAT ACCCATACGA TGTCAATCAG ACTGGAGTCC
 801  GGAAGGACAA GCGGAATCTG GTGCAGGAGT GGCAGGCCAA GCACCAGGGA
 851  GCCCAGTATG TGTGGAACCG CACGGAGCTC CTTCAGGCAG CCAATGACCC
 901  CAGTGTAACA CACCTCATGG GCCTCTTTGA GCCGGCAGAC ATGAAGTATA
 951  ATGTTCAGCA AGACCCCACC AAGGACCCGA CCCTGGAGGA GATGACGGAG
1001  GCGGCCCTGC AAGTGCTGAG CAGGAACCCC AGGGCTTCT ACCTCTTCGT
1051  GGAGGGAGGC CGCATTGACC ACGGTCACCA TGAAGGCAAA GCTTATATGG
1101  CACTGACTGA TACAGTCATG TTTGACAATG CCATCGCCAA GGCTAACGAG
1151  CTCACTAGCG AACTGGACAC GCTGATCCTT GCCACTGCAG ACCACTCCCA
1201  TGTCTTCTCT TTTGGTGGCT ACACACTGCG TGGGACCTCC ATTTTCGGTC
```

Figure 5/2

```
1251  TGGCCCCCAG CAAGGCCTCA GACAACAAGT CCTACACCTC CATCCTCTAT
1301  GGCAATGGCC CTGGCTACGT GCTTGGTGGG GGCTTAAGGC CCGATGTTAA
1351  TGACAGCATA AGCGAGGACC CCTCGTACCG GCAGCAGGCG GCCGTGCCCC
1401  TGTCTAGTGA GTCCCACGGG GGCGAGGACG TGGCGGTGTT CGCGCGAGGC
1451  CCGCAGGCGC ACCTGGTGCA CGGCGTGCAG GAGGAGACCT TCGTGGCGCA
1501  CGTCATGGCC TTTGCGGGCT GCGTGGAGCC CTACACCGAC TGCAATCTGC
1551  CGGCCCCCTC TGGCCTCTCC GACGCCGCGC ACCTGGCGGC CAGCCCGCCT
1601  TCGCTGGCGC TGCTGGCCGG GGCGATGCTG CTGCTGCTGG CGCCTGCCTT
1651  GTACTGACCC CCACCAACTC CAGGTCTTGG GGTTTCCTGC TTTCCTGCCA
1701  AAAATCTCCC AGCGCAGACC CCACCAGAGC TACCACCTCG GAGTCTCCAC
1751  CCTGAAGTCC TATCTTAGCG GCCACTCCCG GATCCCCGAC CAGGCCCCAC
1801  TAGCAGAGCT TCACCTCCCA GAAATGAAGG ATTCACCTTC CAGCAACGAA
1851  GAAGCCTCAG CTCACAGCCC TTCATGGCCC AGCCCATCCA GAGGCTGAGG
1901  CCCTGATTTC CCTGTGACAC CCGTAGACCT ACTGCCCGAC CCCAACTTCA
1951  GTGGCTTGGG ATTTTGTGTT CTGCCACCCC TAACCCCAGT AAGGGGGCTC
2001  GGACCATCCA GACTCTCCCC ACTGCCCACA ACCCCACCTG AGAACCAGGC
2051  TAGCACGGTC CCAAGGTTCC CAGGCCCGGC TAGAACCCAC ACCATGCCTT
2101  TCAGGAGACC CTGGGGCTCC GGGGTTTCCG GGAGGCGTGG CTTTCTTAGG
2151  AGGCGTGGAA ACTGAGGAGG CACGGTTTCT GAGGAGGCGT GCGTCCTGGG
2201  GAGCTGTGGC TTCCGGTCCT CCCCATGCCC TGTGGGCTCC TCCCTAACCA
2251  AGGAGACGGC CAAGGAGACG TCTGGAACCA GGAGCGGCGG GGGAACCTTG
2301  CAGAGCCCTC AGCAACCCCT CCTAGGAACC CAGGGTACCG TTAGAGAGAG
2351  GAGACAGCGA CACAGAGGAG AGGAGACTTG TCCCAGGTCT CTCAGCTGCT
2401  ATGAAGGTGG CCCCGGTGCC CCTTCCAGGC TGGGAGATCC CAGGAGCAGC
2451  GGGGGAGCTG GTGGGTGGGG ACACAGCCCC GCCTTCATGG GAGGGAGGAA
2501  GCAGCCCTCA AATAAACTGT TCTAAGTGTG AAAAAATCTA GA
```

Figure 6

```
  1  FIPAEEEDPA  FWNRQAAQAL  DVAKKLQPIQ  TAAKNVILFL  GDGMGVPTVT
 51  ATRILKGQMN  GKLGPETPLA  MDQFPYVALS  KTYNVDRQVP  DSAGTATAYL
101  CGVKGNYKTI  GVSAAARYNQ  CNTTSGNEVT  SVMNRAKKAG  KSVGVVTTSR
151  VQHASPAGAY  AHTVNRNWYS  DADLPADAQT  YGCQDIATQL  VNNMDIDVIL
201  GGGRMYMFPE  GTPDPEYPYD  VNQTGVRKDK  RNLVQEWQAK  HQGAQYVWNR
251  TELLQAANDP  SVTHLMGLFE  PADMKYNVQQ  DPTKDPTLEE  MTEAALQVLS
301  RNPQGFYLFV  EGGRIDHGHH  EGKAYMALTD  TVMFDNAIAK  ANELTSELDT
351  LILATADHSH  VFSFGGYTLR  GTSIFGLAPS  KASDNKSYTS  ILYGNPGYV
401  LGGGLRPDVN  DSISEDPSYR  QQAAVPLSSE  SHGGEDVAVF  ARGPQAHLVH
451  GVQEETFVAH  VMAFAGCVEP  YTDCNLPAPS  GLSDAAHLAA  SPPSLALLAG
501  AMLLLLAPAL  Y
```

Figure 7

| Residue # | 1 | 2 | 4 | 8 | 31 | 61 | 108 | 122 | 125 | 133 | 142 | 149 | 167 | 180 | 181 | 188 | 192 | 205 | 210 |
|---|---|---|---|---|---|---|---|---|---|---|---|---|---|---|---|---|---|---|---|
| bIAP I   | L | V | V | D | T | G | R | K | R | M | T | N | M | N | A | K | V |   |   |
| bIAP II  | L | I | A | N | T | G | R | N | R | S | T | N | K | N | A | Y | M | E |   |
| bIAP III | F | I | V | D | K | D | R | N | R | I | A | D | T | K | T | N | K | E |   |
| bIAP IV  | F | A | A | D | T | G | K | N | S | M | S | N | T | T | T | N | M | E |   |
|          |   |   |   |   |   |   |   |   |   |   |   |   |   |   |   |   |   |   | * |

| Residue # | 219 | 221 | 222 | 223 | 224 | 231 | 236 | 252 | 258 | 260 | 282 | 289 | 294 | 297 | 299 | 304 | 321 | 322 | 330 |
|---|---|---|---|---|---|---|---|---|---|---|---|---|---|---|---|---|---|---|---|
| bIAP I   | D | A | S | V | N | Q | A | A | D | S | H | Q | V | R | V | R | D | D | E |
| bIAP II  | D | A | S | V | N | Q | E | A | D | S | H | A | A | Q | L | R | D | G | E |
| bIAP III | H | A | A | V | N | R | E | E | N | P | P | E | A | Q | L | Q | D | S | E |
| bIAP IV  | Y | V | V | Q | T | R | R | E | E | N | P | E | A | Q | L | Q | D | G | D |
|          |   |   |   |   |   |   |   |   |   |   |   |   |   |   |   |   |   |   | * |

| Residue # | 331 | 332 | 354 | 380 | 383 | 385 | 400 | 405 | 411 | 413 | 416 | 420 | 427 | 428 | 431 | 453 | 461 | 480 |
|---|---|---|---|---|---|---|---|---|---|---|---|---|---|---|---|---|---|---|
| bIAP I   | A | G | V | S | L | S | A | S | D | T | D | Q | Q | A | E | E | I | T |
| bIAP II  | A | I | V | G | L | S | A | S | G | T | E | R | L | T | T | Q | I | A |
| bIAP III | A | V | V | S | S | K | V | L | D | D | D | R | L | S | S | Q | V | S |
| bIAP IV  | T | V | A |   |   | N | V |   |   |   |   |   |   |   |   |   | V | S |
|          |   |   |   |   |   |   |   |   |   |   |   |   |   |   |   |   |   | * |

Figure 8/1

Ligation reactions to generate constructs

| Construct | original bIAPs in fragment | PCR number (template) | Fragment Origin (PCR or cDNA) | Relevant residues in fragment | Restriction Enzymes | 5' cohesive termini | 3' cohesive termini |
|---|---|---|---|---|---|---|---|
| LIN8bIAP | IV | 1 (IV) | KS – 1 L | 1, 2, 4 | EcoRI – BsaI | AATT | CAGC |
| | IV | 2 (IV) | 8N – 122 | 8, 31 | BsaI – BamHI | GCTG | GATC |
| | I | | 1 | 61, 149, 167, 181, 188, 219, 221, 222, 223, 224, 231, 252, 258, 260, 282, 383, 385, 400, 405, 413, 461 | BamHI – XbaI | GATC | CTAG |
| | | | pcDNA-3 | | XbaI – EcoRI | CTAG | AATT |
| INT1 | IV,I | | LIN8bIAP | | EcoRI – NcoI | AATT | CATG |
| | III | 3 (III) | 1s – M133I | 108, 122, 125, 133 | NcoI – BsaI | CATG | TTCT |
| | I | 4 (I) | S142A – 180 | 142, | BsaI – BsaI | AGAA | TGCA |
| | I | 5 (I) | M180K – K205M | 180, 205 | BsaI – BsaI | TGCA | AACA |
| | I | 6 (I) | V210E – A236E | 210, 236 | BsaI – BsaI | TGTT | TGCC |
| | I | 7 (I) | 236 – 289 | | BsaI – BsaI | GGCA | GGGT |
| | IV | 8 (IV) | E289A – 330 | 289, 294, 297, 299, 322 | BsaI – BsaI | ACCC | TCAG |
| | III | 9 (III) | E330,V332I – Xia | 330, 331, 332, 354 | BsaI - StuI | CTGA | blunt |
| | | | 1 | | StuI - XbaI | blunt | CTAG |
| | I | | pcDNA-3 | | XbaI - EcoRI | CTAG | AATT |

Figure 8/2

| | | | | | | 5' | 3'ACGT5' |
|---|---|---|---|---|---|---|---|
| INT2 | IV,I,III,IV,III | | INT1 | | EcoRI - PstI | AATT | blunt |
| | III | 10 (INT1) | N192Y - S380G | 380 | PstI - StuI | 3'ACGT5' | CTTG |
| | I | 11 (INT1) | N192Y - D411G | 411 | StuI - BsaI | blunt | CTAG |
| | III | 12 (III) | D416E - S428A | 416, 428 | BsaI - BsaI | CAAG | TCCT |
| | | | III | 431, 453 | BsaI - BsaI | CTAG | GTGG |
| | I | 13 (INT1) | D416E - T480S | 480 | BsaI - BsaI | AGGA | GGAT |
| | | 14 (INT1) | 480 - SP6 | | BsaI - BsaI | CCAC | GGCC |
| | | | I | | BsaI - NotI | ATCC | AATT |
| | | | pcDNA-3 | | NotI - EcoRI | GGCC | |
| | | | | | | | |
| INT 3 | IV,I,III,I | | INT2 | | EcoRI - NcoI | AATT | CATG |
| | III,I | | INT2 | | NcoI - PvuII | CATG | blunt |
| | I | 10 (INT1) | N192Y - S380G | 192 | PvuII - EagI | blunt | GGCC |
| | I,IV | | INT2 | | EagI - HindIII | GGCC | AGCT |
| | IV,III,I,III,I | | INT2 | | HindIII - XbaI | AGCT | CTAG |
| | | | pcDNA-3 | | XbaI - EcoRI | CTAG | AATT |
| | | | | | | | |
| bIAP II | IV,I,III,I | | INT 3 | | EcoRI - EagI | AATT | GGCC |
| | I,IV | 15 (INT2) | 236 - Q304R- | 304 | EagI - SmaI | GGCC | blunt |
| | IV | 16 (INT2) | Q304R+ - E321D | 321 | SmaI - HindIII | blunt | AGCT |
| | IV,III,I,III,I | | INT 3 | | HindIII - XbaI | AGCT | CTAG |
| | | | pcDNA-3 | | XbaI - EcoRI | CTAG | AATT |

Figure 9

| AP mutant | $V_{max} \pm sd$ | $V_{max}$ [U/mg] | $T_{50}$ (10 min) |
|---|---|---|---|
| *Wild-type* | | | |
| bIAP I | 5.26 ±0.44 | 2.723 ± 249 | 66,2 |
| bIAP II | 16.61 ±0.88 | 8.600 ± 843 | 58,8 |
| bIAP III | 9.07 ±0.79 | 4.696 ± 494 | 59,1 |
| bIAP IV | 13.11 ±0.85 | 6.787 ± 571 | 52,9 |
| *Chimaeric* | | | |
| L1N8 | 5.90 ±0.40 | 3.055 ± 336 | 65,8 |
| INT 1 | 19.22 ±1.08 | 9.951±1.565 | 59,7 |
| INT 2 | 16.95 ±0.95 | 8.776±1.431 | 55,6 |
| INT 3 | 17.17 ±0.90 | 8.890 ±1.413 | 57,9 |
| *Mutants* | | | |
| [K$^{122}$]bIAP II | 16.21 ±2.33 | 8.393±1.328 | 58,0 |
| [M$^{133}$]bIAP II | 17.69 ±1.45 | 9.159±1.099 | 58,1 |
| [S$^{142}$]bIAP II | 16.53 ±1.06 | 8.559 ± 603 | 57,9 |
| [M$^{180}$]bIAP II | 17.81 ±0.80 | 10.433± 900 | 58,6 |
| [K$^{205}$]bIAP II | 20.29 ±1.25 | 9.454 ± 819 | 57,5 |
| [V$^{210}$]bIAP II | 17.98 ±1.40 | 8.377 ± 908 | 58,1 |
| [A$^{236}$]bIAP II | 19.61 ±2.81 | 10.153±1.565 | 58,1 |
| [QVRV]bIAP II | 19.25 ±0.99 | 9.967 ± 534 | 59,0 |
| [D$^{322}$]bIAP II | 5.44 ±0.34 | 2.817 ± 307 | 61,4 |
| [G$^{332}$]bIAP II | 16.53 ±1.30 | 8.559±1.075 | 59,2 |
| [G$^{322}$]bIAP I | 19.60 ±0.99 | 10.148±1.021 | 60,6 |

SEQUENCE LISTING (1) GENERAL INFORMATION:

(iii) NUMBER OF SEQUENCES: 54

(2) INFORMATION FOR SEQ ID NO: 1:

(i) SEQUENCE CHARACTERISTICS:
      (A) LENGTH: 1798 base pairs
      (B) TYPE: nucleotide
      (C) STRANDEDNESS: single strand
      (D) TOPOLOGY: linear (ii) MOLECULE TYPE: genomic DNA (xi) SEQUENCE DESCRIPTION: SEQ ID NO: 1:

GAATTCGGCA CGAGCCAGGT CCCATCCTGA CCCTCCGCCA TCACACAGCT ATGCAGTGGG    60

```
CCTGTGTGCT GCTGCTGCTG GGCCTGTGGC TACAGCTCTC CCTCACCCTC ATCCCAGCTG    120

AGGAGGAAAA CCCCGCCTTC TGGAACCGCC AGGCAGCCCA GGCCCTTGAT GTAGCCAAGA    180

AGTTGCAGCC GATCCAGACA GCTGCCAAGA ATGTCATCCT CTTCTTGGGG GATGGGATGG    240

GGGTGCCTAC GGTGACAGCC ACTCGGATCC TAAAGGGGCA GATGAATGGC AAACTGGGAC    300

CTGAGACACC CCTGGCCATG GACCAGTTCC CATACGTGGC TCTGTCCAAG ACATACAACG    360

TGGACAGACA GGTGCCAGAC AGCGCAGGCA CTGCCACTGC CTACCTGTGT GGGGTCAAGG    420

GCAACTACAG AACCATCGGT GTAAGTGCAG CCGCCCGCTA CAATCAGTGC AACACGACAC    480

GTGGGAATGA GGTCACGTCT GTGATCAACC GGGCCAAGAA AGCAGGGAAG GCCGTGGGAG    540

TGGTGACCAC CACCAGGGTG CAGCATGCCT CCCCAGCCGG GGCCTACGCG CACACGGTGA    600

ACCGAAACTG GTACTCAGAC GCCGACCTGC CTGCTGATGC ACAGAAGAAT GGCTGCCAGG    660

ACATCGCCGC ACAGCTGGTC TACAACATGG ATATTGACGT GATCCTGGGT GGAGGCCGAA    720

TGTACATGTT TCCTGAGGGG ACCCCAGACC CTGAATACCC AGATGATGCC AGTGTGAATG    780

GAGTCCGGAA GGACAAGCAG AACCTGGTGC AGGAATGGCA GGCCAAGCAC CAGGGAGCCC    840

AGTATGTGTG GAACCGCACT GCGCTCCTTC AGGCGGCCGA TGACTCCAGT GTAACACACC    900

TCATGGGCCT CTTTGAGCCG GCAGACATGA AGTATAATGT TCAGCAAGAC CACACCAAGG    960

ACCCGACCCT GGCGGAGATG ACGGAGGCGG CCCTGCAAGT GCTGAGCAGG AACCCCCGGG   1020

GCTTCTACCT CTTCGTGGAG GGAGGCCGCA TTGACCACGG TCACCATGAC GGCAAAGCTT   1080

ATATGGCACT GACTGAGGCG ATCATGTTTG ACAATGCCAT CGCCAAGGCT AACGAGCTCA   1140

CTAGCGAACT GGACACGCTG ATCCTTGTCA CTGCAGACCA CTCCCATGTC TTCTCTTTTG   1200

GTGGCTACAC ACTGCGTGGG ACCTCCATTT TCGGTCTGGC CCCCGGCAAG GCCTTAGACA   1260

GCAAGTCCTA CACCTCCATC CTCTATGGCA ATGGCCCAGG CTATGCGCTT GGCGGGGGCT   1320

CGAGGCCCGA TGTTAATGGC AGCACAAGCG AGGAACCCTC ATACCGGCAG CAGGCGGCCG   1380

TGCCCCTGGC TAGCGAGACC CACGGGGGCG AAGACGTGGC GGTGTTCGCG CGAGGCCCGC   1440

AGGCGCACCT GGTGCACGGC GTGCAGGAGG AGACCTTCGT GGCGCACATC ATGGCCTTTG   1500

CGGGCTGCGT GGAGCCCTAC ACCGACTGCA ATCTGCCAGC CCCCGCCACC GCCACCAGCA   1560

TCCCCGACGC CGCGCACCTG GCGGCCAGCC CGCCTCCACT GGCGCTGCTG GCTGGGGCGA   1620

TGCTGCTGCT GCTGGCGCCC ACCTTGTACT AACCCCCACC AGTTCCAGGT CTCGGGATTT   1680

CCCGCTCTCC TGCCCAAAAC CTCCCAGCTC AGGCCCTACC GGAGCTACCA CCTCAGAGTC   1740

CCCACCCCGA AGTGCTATCC TAGCTGCCAC TCCTGCAGAC CCGACCCAGC CGGAATTC     1798
```

(2) INFORMATION FOR SEQ ID NO: 2:

(i) SEQUENCE CHARACTERISTICS:
        (A) LENGTH: 480 amino acids
        (B) TYPE: amino acid
        (C) STRANDEDNESS: single strand
        (D) TOPOLOGY: linear (ii) MOLECULE TYPE: protein (xi) SEQUENCE DESCRIPTION: SEQ ID NO: 2:

```
Leu Ile Pro Ala Glu Glu Glu Asn Pro Ala Phe Trp Asn Arg Gln Ala
1               5                   10                  15

Ala Gln Ala Leu Asp Val Ala Lys Lys Leu Gln Pro Ile Gln Thr Ala
            20                  25                  30

Ala Lys Asn Val Ile Leu Phe Leu Gly Asp Gly Met Gly Val Pro Thr
```

```
                35                  40                  45
Val Thr Ala Thr Arg Ile Leu Lys Gly Gln Met Asn Gly Lys Leu Gly
 50                  55                  60

Pro Glu Thr Pro Leu Ala Met Asp Gln Phe Pro Tyr Val Ala Leu Ser
65                  70                  75                  80

Lys Thr Tyr Asn Val Asp Arg Gln Val Pro Asp Ser Ala Gly Thr Ala
                 85                  90                  95

Thr Ala Tyr Leu Cys Gly Val Lys Gly Asn Tyr Arg Thr Ile Gly Val
            100                 105                 110

Ser Ala Ala Arg Tyr Asn Gln Cys Asn Thr Thr Arg Gly Asn Glu
        115                 120                 125

Val Thr Ser Val Ile Asn Arg Ala Lys Lys Ala Gly Lys Ala Val Gly
    130                 135                 140

Val Val Thr Thr Thr Arg Val Gln His Ala Ser Pro Ala Gly Ala Tyr
145                 150                 155                 160

Ala His Thr Val Asn Arg Asn Trp Tyr Ser Asp Ala Asp Leu Pro Ala
                165                 170                 175

Asp Ala Gln Lys Asn Gly Cys Gln Asp Ile Ala Ala Gln Leu Val Tyr
            180                 185                 190

Asn Met Asp Ile Asp Val Ile Leu Gly Gly Gly Arg Met Tyr Met Phe
        195                 200                 205

Pro Glu Gly Thr Pro Asp Pro Glu Tyr Pro Asp Asp Ala Ser Val Asn
    210                 215                 220

Gly Val Arg Lys Asp Lys Gln Asn Leu Val Gln Glu Trp Gln Ala Lys
225                 230                 235                 240

His Gln Gly Ala Gln Tyr Val Trp Asn Arg Thr Ala Leu Leu Gln Ala
                245                 250                 255

Ala Asp Asp Ser Ser Val Thr His Leu Met Gly Leu Phe Glu Pro Ala
            260                 265                 270

Asp Met Lys Tyr Asn Val Gln Gln Asp His Thr Lys Asp Pro Thr Leu
        275                 280                 285

Ala Glu Met Thr Glu Ala Ala Leu Gln Val Leu Ser Arg Asn Pro Arg
    290                 295                 300

Gly Phe Tyr Leu Phe Val Glu Gly Gly Arg Ile Asp His Gly His His
305                 310                 315                 320

Asp Gly Lys Ala Tyr Met Ala Leu Thr Glu Ala Ile Met Phe Asp Asn
                325                 330                 335

Ala Ile Ala Lys Ala Asn Glu Leu Thr Ser Glu Leu Asp Thr Leu Ile
            340                 345                 350

Leu Val Thr Ala Asp His Ser His Val Phe Ser Phe Gly Gly Tyr Thr
        355                 360                 365

Leu Arg Gly Thr Ser Ile Phe Gly Leu Ala Pro Gly Lys Ala Leu Asp
    370                 375                 380

Ser Lys Ser Tyr Thr Ser Ile Leu Tyr Gly Asn Gly Pro Gly Tyr Ala
385                 390                 395                 400

Leu Gly Gly Gly Ser Arg Pro Asp Val Asn Gly Ser Thr Ser Glu Glu
                405                 410                 415

Pro Ser Tyr Arg Gln Gln Ala Ala Val Pro Leu Ala Ser Glu Thr His
            420                 425                 430

Gly Gly Glu Asp Val Ala Val Phe Ala Arg Gly Pro Gln Ala His Leu
        435                 440                 445

Val His Gly Val Gln Glu Glu Thr Phe Val Ala His Ile Met Ala Phe
    450                 455                 460
```

Ala Gly Cys Val Glu Pro Tyr Thr Asp Cys Asn Leu Pro Ala Pro Ala
465                 470                 475                 480

(2) INFORMATION FOR SEQ ID NO: 3:

(i) SEQUENCE CHARACTERISTICS:
        (A) LENGTH: 2460 base pairs
        (B) TYPE: nucleotide
        (C) STRANDEDNESS: single strand
        (D) TOPOLOGY: linear (ii) MOLECULE TYPE: genomic DNA (xi) SEQUENCE DESCRIPTION: SEQ ID NO: 3:

```
GAATTCGGCA CGAGCGAGAC CCAGACTCCC CAGGTCCCAT CCTGACCCTC CGCCATCACA      60

CAGCTATGCA GGGGGCCTGC GTGCTGCTGC TGCTGGGCCT GTGGCTACAG CTCTCCCTCG     120

CCTTCATCCC AGTTGAGGAG GAAGACCCCG CCTTCTGGAA CCGCCAGGCA GCCCAGGCCC     180

TTGATGTGGC TAAGAAGCTG CAGCCCATCC AGAAAGCCGC CAAGAATGTC ATCCTCTTCT     240

TGGGAGATGG GATGGGGGTG CCTACGGTGA CAGCCACTCG GATACTGAAG GGCAGATGA      300

ATGACAAGCT GGGACCTGAG ACACCCCTGG CCATGGACCA GTTCCCATAC GTGGCTCTGT     360

CCAAGACATA CAACGTGGAC AGACAGGTGC AGACAGCGC AGGCACTGCC ACTGCCTACC      420

TGTGTGGGGT CAAGGGCAAC TACAGAACCA TCGGTGTAAG TGCAGCCGCC CGCTACAATC     480

AGTGCAACAC GACACGTGGG AATGAGGTCA CGTCTGTGAT GAACCGGGCC AAGAAAGCAG     540

GGAAGTCAGT GGGAGTGGTG ACCACCACCA GGGTGCAGCA CGCCTCCCCA GCCGGTGCTT     600

ATGCACACAC GGTGAACCGT GACTGGTACT CAGACGCCGA CCTGCCTGCC GATGCACAGA     660

CGTATGGCTG CCAGGACATC GCCACACAAC TGGTCAACAA CATGGATATT GACGTGATCC     720

TGGGTGGAGG CCGAAAGTAC ATGTTTCCTG AGGGGACCCC AGACCCTGAA TACCCACACG     780

ATGCCAGTGT GAATGGAGTC CGGAAGGACA AGCGGAATCT GGTGCAGGAG TGGCAGGCCA     840

AGCACCAGGA AGCCCAGTAT GTGTGGAACC GCACGGAGCT CCTTCAGGCA GCCAATGACT     900

CCAGTGTTAC ACATCTCATG GGCCTCTTTG AGCCGGCAGA CATGAAGTAT AATGTTCAGC     960

AAGACCCCAC CAAGGACCCG ACCCTGGAGG AGATGACGGA GGCGGCCCTG CAAGTGCTGA    1020

GCAGGAACCC CCAGGGCTTC TACCTCTTCG TGGAGGGAGG CCGCATTGAC CACGGTCACC    1080

ATGATAGCAA AGCTTATATG GCGCTGACTG AGGCGGTCAT GTTTGACAAT GCCATCGCCA    1140

AGGCTAACGA GCTCACTAGC GAACTGGACA CGCTGATCCT TGTCACTGCA GACCACTCCC    1200

ATGTCTTCTC TTTTGGTGGC TACACACTGC GTGGGACCTC CATTTTCGGT CTGGCCCCCA    1260

GCAAGGCCTC AGACAAGAAG TCCTACACCT CCATCCTCTA TGGCAATGGC CCTGGCTACG    1320

TGCTTGGTGG GGGCTCAAGG CCCGATGTTA ATGACAGCAT AAGCGAGGAC CCCTCATACC    1380

GGCAGCAGGC GGCCGTGCCC CTGTCTAGCG AGACCCACGG GGGCGAAGAC GTGGCGGTGT    1440

TCGCGCGAGG CCCGCAGGCG CACCTGGTGC ACGGCGTGCA GGAGGAGACC TTCGTGGCGC    1500

ACGTCATGGC CTTTGCGGGC TGCGTGGAGC CCTACACCGA CTGCAATCTG CCGGCCCCCT    1560

CTGGCCTCTC CGACGCCGCG CACCTGGCGG CCAGCGCGCC TTCGCTAGCG CTGCTGGCCG    1620

GGGCGATGCT GCTGCTGCTG GCGCCCGCCT TGTACTGACC CCACCAACT CCAGGTCTTG     1680

GGGTTTCCCG CTTTCTTGCC CCAAAATCTC CCAGCGCAGG CCCCATCTGA GCTACCACCT    1740

CAGAGTCCCC ACCCTGAAGT CCTATCTAGC GCACTCCAGA CCGCGACTCA GCCCCACCAC    1800

CAGAGCTTCA CCTCCCAGCA ACGAAGGAGC CTTAGCTCAC AGCCTTTCAT GGCCCAGACC    1860
```

```
ATTCTGGAGA CTGAGGCCCT GATTTTCCCG ACCCAACTTC AGTGGCTTGA GATTTTGTGT    1920

TCTGCCACCC CGGATCCCTG TAAGGGGGCT CGGACCATCC AGACTCCCCC CACTGCCCAC    1980

AGCCGAACCT GAGGACCAGG CTGGCACGGT CCCAGGGGTC CCAGGCCCGG CTGGAACCCA    2040

CATCTTTGCC TTTCAGGAGA CCCTGGGACT GTGGGGTTTC AGGAGGCGT GGCTTCTTGG    2100

AGGCGTGGCT TCGGAGGGGT GGCTTCCGAG AAGGCGTGGC TCCCTGTCCT GGAACCACCC    2160

TGTGGGNATC TGGGGCCCAA GGAGATGTCT GGGGCAAAGA GTGCCGGGGG ACCCTGGACA    2220

CAGAATCTTC AGCGGCCCCT CCTAGGAACC CAGCAGTACC ATTATAGAGA GGGGACACCG    2280

ACACAGAGGA GAGGAGACTT GTCCCAGGTC CCTCAGCTGC TGTGAGGGGT GACCCTTGGT    2340

TCCCGTTACC AGGCTGGGGG ATCCCAGGAG CAGCGGGGGA CCTGGGGGTG GGGACACAGG    2400

CCCCACACTC CTGGGAGGGA GGAAGCAGCC CTNAAATAAA CTGTTCCTCG TGCCGAATTC    2460
```

(2) INFORMATION FOR SEQ ID NO: 4:

(i) SEQUENCE CHARACTERISTICS:
        (A) LENGTH: 511 amino acids
        (B) TYPE: amino acid
        (C) STRANDEDNESS: single strand
        (D) TOPOLOGY: linear (ii) MOLECULE TYPE: protein (xi) SEQUENCE DESCRIPTION: SEQ ID NO: 4:

```
Phe Ile Pro Val Glu Glu Asp Pro Ala Phe Trp Asn Arg Gln Ala
1               5                  10                  15

Ala Gln Ala Leu Asp Val Ala Lys Lys Leu Gln Pro Ile Gln Lys Ala
            20                  25                  30

Ala Lys Asn Val Ile Leu Phe Leu Gly Asp Gly Met Gly Val Pro Thr
        35                  40                  45

Val Thr Ala Thr Arg Ile Leu Lys Gly Gln Met Asn Asp Lys Leu Gly
    50                  55                  60

Pro Glu Thr Pro Leu Ala Met Asp Gln Phe Pro Tyr Val Ala Leu Ser
65                  70                  75                  80

Lys Thr Tyr Asn Val Asp Arg Gln Val Pro Asp Ser Ala Gly Thr Ala
                85                  90                  95

Thr Ala Tyr Leu Cys Gly Val Lys Gly Asn Tyr Arg Thr Ile Gly Val
            100                 105                 110

Ser Ala Ala Ala Arg Tyr Asn Gln Cys Asn Thr Thr Arg Gly Asn Glu
        115                 120                 125

Val Thr Ser Val Met Asn Arg Ala Lys Lys Ala Gly Lys Ser Val Gly
    130                 135                 140

Val Val Thr Thr Thr Arg Val Gln His Ala Ser Pro Ala Gly Ala Tyr
145                 150                 155                 160

Ala His Thr Val Asn Arg Asp Trp Tyr Ser Asp Ala Asp Leu Pro Ala
                165                 170                 175

Asp Ala Gln Thr Tyr Gly Cys Gln Asp Ile Ala Thr Gln Leu Val Asn
            180                 185                 190

Asn Met Asp Ile Asp Val Ile Leu Gly Gly Gly Arg Lys Tyr Met Phe
        195                 200                 205

Pro Glu Gly Thr Pro Asp Pro Glu Tyr Pro His Asp Ala Ser Val Asn
    210                 215                 220

Gly Val Arg Lys Asp Lys Arg Asn Leu Val Gln Glu Trp Gln Ala Lys
225                 230                 235                 240

His Gln Gly Ala Gln Tyr Val Trp Asn Arg Thr Glu Leu Leu Gln Ala
```

```
                    245                 250                 255
Ala Asn Asp Ser Ser Val Thr His Leu Met Gly Leu Phe Glu Pro Ala
                260                 265                 270

Asp Met Lys Tyr Asn Val Gln Gln Asp Pro Thr Lys Asp Pro Thr Leu
            275                 280                 285

Glu Glu Met Thr Glu Ala Ala Leu Gln Val Leu Ser Arg Asn Pro Gln
        290                 295                 300

Gly Phe Tyr Leu Phe Val Glu Gly Gly Arg Ile Asp His Gly His His
305                 310                 315                 320

Asp Ser Lys Ala Tyr Met Ala Leu Thr Glu Ala Val Met Phe Asp Asn
                325                 330                 335

Ala Ile Ala Lys Ala Asn Glu Leu Thr Ser Glu Leu Asp Thr Leu Ile
                340                 345                 350

Leu Val Thr Ala Asp His Ser His Val Phe Ser Phe Gly Gly Tyr Thr
                355                 360                 365

Leu Arg Gly Thr Ser Ile Phe Gly Leu Ala Pro Ser Lys Ala Ser Asp
            370                 375                 380

Lys Lys Ser Tyr Thr Ser Ile Leu Tyr Gly Asn Gly Pro Gly Tyr Val
385                 390                 395                 400

Leu Gly Gly Gly Ser Arg Pro Asp Val Asn Asp Ser Ile Ser Glu Asp
                405                 410                 415

Pro Ser Tyr Arg Gln Gln Ala Ala Val Pro Leu Ser Ser Glu Thr His
                420                 425                 430

Gly Gly Glu Asp Val Ala Val Phe Ala Arg Gly Pro Gln Ala His Leu
            435                 440                 445

Val His Gly Val Gln Glu Thr Phe Val Ala His Val Met Ala Phe
            450                 455                 460

Ala Gly Cys Val Glu Pro Tyr Thr Asp Cys Asn Leu Pro Ala Pro Ser
465                 470                 475                 480

Gly Leu Ser Asp Ala Ala His Leu Ala Ala Ser Ala Pro Ser Leu Ala
                485                 490                 495

Leu Leu Ala Gly Ala Met Leu Leu Leu Leu Ala Pro Ala Leu Tyr
            500                 505                 510

(2) INFORMATION FOR SEQ ID NO: 5:

(i) SEQUENCE CHARACTERISTICS:
        (A) LENGTH: 2542 base pairs
        (B) TYPE: nucleotide
        (C) STRANDEDNESS: single strand
        (D) TOPOLOGY: linear (ii) MOLECULE TYPE: genomic DNA (xi) SEQUENCE DESCRIPTION: SEQ ID NO: 5:

GAATTCGGCA CGAGGAGACC CGGCCTCCCC AGGTCCCATC CTGACCCTCC GCCATCACAC     60

AGCCATGCAG TGGGCCTGTG TGCTGCTGCT GCTGGGCCTG TGGCTACAGC TCTCCCTCAC    120

CTTCATCCCA GCTGAGGAGG AAGACCCCGC CTTCTGGAAC CGCCAGGCAG CCCAGGCCCT    180

TGATGTAGCC AAGAAGTTGC AGCCGATCCA GACAGCTGCC AAGAATGTCA TCCTCTTCTT    240

GGGGGATGGG ATGGGGGTGC CTACGGTGAC AGCCACTCGG ATCCTAAAGG GGCAGATGAA    300

TGGTAAGCTG GACCTGAGAC ACCCCTGGCC CATGGACCAG TTCCCATACG TGGCTCTGTC    360

CAAGACATAC AACGTGGACA GACAGGTGCC AGACAGCGCA GGCACTGCCA CTGCCTACCT    420

GTGTGGGGTC AAGGGCAACT ACAAAACCAT TGGTGTAAGT GCAGCCGCCC GCTACAACCA    480
```

-continued

```
GTGCAACACA CAAGTGGCA ATGAGGTCAC GTCTGTGATG AACCGGGCCA AGAAAGCAGG    540

AAAGTCAGTG GGAGTGGTGA CCACCTCCAG GGTGCAGCAT GCCTCCCCAG CCGGTGCTTA    600

TGCACACACG GTGAACCGAA ACTGGTACTC AGATGCCGAC CTGCCTGCCG ATGCACAGAC    660

GTATGGCTGC CAGGACATCG CCACACAACT GGTCAACAAC ATGGATATTG ACGTGATCCT    720

GGGTGGAGGC CGAATGTACA TGTTTCCTGA GGGGACCCCG GATCCTGAAT ACCCATACGA    780

TGTCAATCAG ACTGGAGTCC GGAAGGACAA GCGGAATCTG GTGCAGGAGT GGCAGGCCAA    840

GCACCAGGGA GCCCAGTATG TGTGGAACCG CACGGAGCTC CTTCAGGCAG CCAATGACCC    900

CAGTGTAACA CACCTCATGG GCCTCTTTGA GCCGGCAGAC ATGAAGTATA ATGTTCAGCA    960

AGACCCCACC AAGGACCCGA CCCTGGAGGA GATGACGGAG GCGGCCCTGC AAGTGCTGAG   1020

CAGGAACCCC CAGGGCTTCT ACCTCTTCGT GGAGGGAGGC CGCATTGACC ACGGTCACCA   1080

TGAAGGCAAA GCTTATATGG CACTGACTGA TACAGTCATG TTTGACAATG CCATCGCCAA   1140

GGCTAACGAG CTCACTAGCG AACTGGACAC GCTGATCCTT GCCACTGCAG ACCACTCCCA   1200

TGTCTTCTCT TTTGGTGGCT ACACACTGCG TGGGACCTCC ATTTTCGGTC TGGCCCCCAG   1260

CAAGGCCTCA GACAACAAGT CCTACACCTC CATCCTCTAT GGCAATGGCC CTGGCTACGT   1320

GCTTGGTGGG GGCTTAAGGC CCGATGTTAA TGACAGCATA AGCGAGGACC CCTCGTACCG   1380

GCAGCAGGCG GCCGTGCCCC TGTCTAGTGA GTCCCACGGG GGCGAGGACG TGGCGGTGTT   1440

CGCGCGAGGC CCGCAGGCGC ACCTGGTGCA CGGCGTGCAG GAGGAGACCT TCGTGGCGCA   1500

CGTCATGGCC TTTGCGGGCT GCGTGGAGCC CTACACCGAC TGCAATCTGC CGGCCCCCTC   1560

TGGCCTCTCC GACGCCGCGC ACCTGGCGGC CAGCCCGCCT TCGCTGGCGC TGCTGGCCGG   1620

GGCGATGCTG CTGCTGCTGG CGCCTGCCTT GTACTGACCC CCACCAACTC CAGGTCTTGG   1680

GGTTTCCTGC TTTCCTGCCA AAAATCTCCC AGCGCAGACC CCACCAGAGC TACCACCTCG   1740

GAGTCTCCAC CCTGAAGTCC TATCTTAGCG GCCACTCCCG GATCCCCGAC CAGGCCCCAC   1800

TAGCAGAGCT TCACCTCCCA GAAATGAAGG ATTCACCTTC CAGCAACGAA GAAGCCTCAG   1860

CTCACAGCCC TTCATGGCCC AGCCCATCCA GAGGCTGAGG CCCTGATTTC CCTGTGACAC   1920

CCGTAGACCT ACTGCCCGAC CCCAACTTCA GTGGCTTGGG ATTTTGTGTT CTGCCACCCC   1980

TAACCCCAGT AAGGGGCTC GGACCATCCA GACTCTCCCC ACTGCCCACA ACCCCACCTG   2040

AGAACCAGGC TAGCACGGTC CCAAGGTTCC CAGGCCCGGC TAGAACCCAC ACCATGCCTT   2100

TCAGGAGACC CTGGGCTCC GGGGTTTCCG GGAGGCGTGG CTTTCTTAGG AGGCGTGGAA   2160

ACTGAGGAGG CACGGTTTCT GAGGAGGCGT GCGTCCTGGG GAGCTGTGGC TTCCGGTCCT   2220

CCCCATGCCC TGTGGGCTCC TCCCTAACCA AGGAGACGGC CAAGGAGACG TCTGGAACCA   2280

GGAGCGGCGG GGGAACCTTG CAGAGCCCTC AGCAACCCCT CCTAGGAACC CAGGGTACCG   2340

TTAGAGAGAG GAGACAGCGA CACAGAGGAG AGGAGACTTG TCCCAGGTCT CTCAGCTGCT   2400

ATGAAGGTGG CCCCGGTGCC CCTTCCAGGC TGGGAGATCC CAGGAGCAGC GGGGGAGCTG   2460

GTGGGTGGGG ACACAGCCCC GCCTTCATGG GAGGGAGGAA GCAGCCCTCA AATAAACTGT   2520

TCTAAGTGTG AAAAAATCTA GA                                           2542
```

(2) INFORMATION FOR SEQ ID NO: 6:

(i) SEQUENCE CHARACTERISTICS:
        (A) LENGTH: 511 amino acids
        (B) TYPE: amino acid
        (C) STRANDEDNESS: single strand
        (D) TOPOLOGY: linear (ii) MOLECULE TYPE: protein (xi) SEQUENCE DESCRIPTION: SEQ ID NO: 6:

```
Phe Ile Pro Ala Glu Glu Asp Pro Ala Phe Trp Asn Arg Gln Ala
1               5                   10                  15

Ala Gln Ala Leu Asp Val Ala Lys Lys Leu Gln Pro Ile Gln Thr Ala
                20                  25                  30

Ala Lys Asn Val Ile Leu Phe Leu Gly Asp Gly Met Gly Val Pro Thr
            35                  40                  45

Val Thr Ala Thr Arg Ile Leu Lys Gly Gln Met Asn Gly Lys Leu Gly
50                  55                  60

Pro Glu Thr Pro Leu Ala Met Asp Gln Phe Pro Tyr Val Ala Leu Ser
65                  70                  75                  80

Lys Thr Tyr Asn Val Asp Arg Gln Val Pro Asp Ser Ala Gly Thr Ala
                85                  90                  95

Thr Ala Tyr Leu Cys Gly Val Lys Gly Asn Tyr Lys Thr Ile Gly Val
            100                 105                 110

Ser Ala Ala Ala Arg Tyr Asn Gln Cys Asn Thr Thr Ser Gly Asn Glu
        115                 120                 125

Val Thr Ser Val Met Asn Arg Ala Lys Lys Ala Gly Lys Ser Val Gly
130                 135                 140

Val Val Thr Thr Ser Arg Val Gln His Ala Ser Pro Ala Gly Ala Tyr
145                 150                 155                 160

Ala His Thr Val Asn Arg Asn Trp Tyr Ser Asp Ala Asp Leu Pro Ala
                165                 170                 175

Asp Ala Gln Thr Tyr Gly Cys Gln Asp Ile Ala Thr Gln Leu Val Asn
            180                 185                 190

Asn Met Asp Ile Asp Val Ile Leu Gly Gly Gly Arg Met Tyr Met Phe
        195                 200                 205

Pro Glu Gly Thr Pro Asp Pro Glu Tyr Pro Tyr Asp Val Asn Gln Thr
210                 215                 220

Gly Val Arg Lys Asp Lys Arg Asn Leu Val Gln Glu Trp Gln Ala Lys
225                 230                 235                 240

His Gln Gly Ala Gln Tyr Val Trp Asn Arg Thr Glu Leu Leu Gln Ala
                245                 250                 255

Ala Asn Asp Pro Ser Val Thr His Leu Met Gly Leu Phe Glu Pro Ala
            260                 265                 270

Asp Met Lys Tyr Asn Val Gln Gln Asp Pro Thr Lys Asp Pro Thr Leu
        275                 280                 285

Glu Glu Met Thr Glu Ala Ala Leu Gln Val Leu Ser Arg Asn Pro Gln
290                 295                 300

Gly Phe Tyr Leu Phe Val Glu Gly Gly Arg Ile Asp His Gly His His
305                 310                 315                 320

Glu Gly Lys Ala Tyr Met Ala Leu Thr Asp Thr Val Met Phe Asp Asn
                325                 330                 335

Ala Ile Ala Lys Ala Asn Glu Leu Thr Ser Glu Leu Asp Thr Leu Ile
            340                 345                 350

Leu Ala Thr Ala Asp His Ser His Val Phe Ser Phe Gly Gly Tyr Thr
        355                 360                 365

Leu Arg Gly Thr Ser Ile Phe Gly Leu Ala Pro Ser Lys Ala Ser Asp
370                 375                 380

Asn Lys Ser Tyr Thr Ser Ile Leu Tyr Gly Asn Gly Pro Gly Tyr Val
385                 390                 395                 400
```

```
Leu Gly Gly Gly Leu Arg Pro Asp Val Asn Asp Ser Ile Ser Glu Asp
                405                 410                 415
Pro Ser Tyr Arg Gln Gln Ala Ala Val Pro Leu Ser Ser Glu Ser His
            420                 425                 430
Gly Gly Glu Asp Val Ala Val Phe Ala Arg Gly Pro Gln Ala His Leu
            435                 440                 445
Val His Gly Val Gln Glu Thr Phe Val Ala His Val Met Ala Phe
    450                 455                 460
Ala Gly Cys Val Glu Pro Tyr Thr Asp Cys Asn Leu Pro Ala Pro Ser
465             470                 475                 480
Gly Leu Ser Asp Ala Ala His Leu Ala Ala Ser Pro Pro Ser Leu Ala
                485                 490                 495
Leu Leu Ala Gly Ala Met Leu Leu Leu Leu Ala Pro Ala Leu Tyr
                500                 505                 510
```

(2) INFORMATION FOR SEQ ID NO: 7:

(i) SEQUENCE CHARACTERISTICS:
        (A) LENGTH: 18 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 7:

GCCAAGAATG TCATCCTC                                    18

(2) INFORMATION FOR SEQ ID NO: 8:

(i) SEQUENCE CHARACTERISTICS:
        (A) LENGTH: 18 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 8:

GAGGATGACA TTCTTGGC                                    18

(2) INFORMATION FOR SEQ ID NO: 9:

(i) SEQUENCE CHARACTERISTICS:
        (A) LENGTH: 17 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 9:

GGTGTAAGTG CAGCCGC                                     17

(2) INFORMATION FOR SEQ ID NO: 10:

(i) SEQUENCE CHARACTERISTICS:
        (A) LENGTH: 17 base pairs
        (B) TYPE: nucleotide
        (C) STRANDEDNESS: single strand
        (D) TOPOLOGY: linear (ii) MOLECULE TYPE: other nucleic acid (A) DESCRIPTION:  /desc = "oligonucleotide"

(xi) SEQUENCE DESCRIPTION: SEQ ID NO: 10:

GCGGCTGCAC TTAGACC                                                      17

(2) INFORMATION FOR SEQ ID NO: 11:

(i) SEQUENCE CHARACTERISTICS:
        (A) LENGTH: 17 base pairs
        (B) TYPE: nucleotide
        (C) STRANDEDNESS: single strand
        (D) TOPOLOGY: linear (ii) MOLECULE TYPE: other nucleic acid
        (A) DESCRIPTION:  /desc = "oligonucleotide"

(xi) SEQUENCE DESCRIPTION: SEQ ID NO: 11:

AATGTACATG TTTCCTG                                                      17

(2) INFORMATION FOR SEQ ID NO: 12:

(i) SEQUENCE CHARACTERISTICS:
        (A) LENGTH: 17 base pairs
        (B) TYPE: nucleotide
        (C) STRANDEDNESS: single strand
        (D) TOPOLOGY: linear (ii) MOLECULE TYPE: other nucleic acid
        (A) DESCRIPTION:  /desc = "oligonucleotide"

(xi) SEQUENCE DESCRIPTION: SEQ ID NO: 12:

CAGGAAACAT GTACATT                                                      17

(2) INFORMATION FOR SEQ ID NO: 13:

(i) SEQUENCE CHARACTERISTICS:
        (A) LENGTH: 18 base pairs
        (B) TYPE: nucleotide
        (C) STRANDEDNESS: single strand
        (D) TOPOLOGY: linear (ii) MOLECULE TYPE: other nucleic acid
        (A) DESCRIPTION:  /desc = "oligonucleotide"

(xi) SEQUENCE DESCRIPTION: SEQ ID NO: 13:

CCAGGGCTTC TACCTCTT                                                     18

(2) INFORMATION FOR SEQ ID NO: 14:

(i) SEQUENCE CHARACTERISTICS:
        (A) LENGTH: 18 base pairs
        (B) TYPE: nucleotide
        (C) STRANDEDNESS: single strand
        (D) TOPOLOGY: linear (ii) MOLECULE TYPE: other nucleic acid
        (A) DESCRIPTION:  /desc = "oligonucleotide"

(xi) SEQUENCE DESCRIPTION: SEQ ID NO: 14:

AAGAGGTAGA AGCCCTGG                                                     18

(2) INFORMATION FOR SEQ ID NO: 15:

(i) SEQUENCE CHARACTERISTICS:
        (A) LENGTH: 18 base pairs
        (B) TYPE: nucleotide
        (C) STRANDEDNESS: single strand
        (D) TOPOLOGY: linear (ii) MOLECULE TYPE: other nucleic acid
             (A) DESCRIPTION:   /desc = "oligonucleotide"

(xi) SEQUENCE DESCRIPTION: SEQ ID NO: 15:

ACCAGAGCTA CCACCTCG                                                          18

(2) INFORMATION FOR SEQ ID NO: 16:

(i) SEQUENCE CHARACTERISTICS:
             (A) LENGTH: 18 base pairs
             (B) TYPE: nucleotide
             (C) STRANDEDNESS: single strand
             (D) TOPOLOGY: linear (ii) MOLECULE TYPE: other nucleic acid
             (A) DESCRIPTION:   /desc = "oligonucleotide"

(xi) SEQUENCE DESCRIPTION: SEQ ID NO: 16:

AAGCAGGAAA CCCCAAGA                                                          18

(2) INFORMATION FOR SEQ ID NO: 17:

(i) SEQUENCE CHARACTERISTICS:
             (A) LENGTH: 18 base pairs
             (B) TYPE: nucleotide
             (C) STRANDEDNESS: single strand
             (D) TOPOLOGY: linear (ii) MOLECULE TYPE: other nucleic acid
             (A) DESCRIPTION:   /desc = "oligonucleotide"

(xi) SEQUENCE DESCRIPTION: SEQ ID NO: 17:

CTTCAGTGGC TTGGGATT                                                          18

(2) INFORMATION FOR SEQ ID NO: 18:

(i) SEQUENCE CHARACTERISTICS:
             (A) LENGTH: 18 base pairs
             (B) TYPE: nucleotide
             (C) STRANDEDNESS: single strand
             (D) TOPOLOGY: linear (ii) MOLECULE TYPE: other nucleic acid
             (A) DESCRIPTION:   /desc = "oligonucleotide"

(xi) SEQUENCE DESCRIPTION: SEQ ID NO: 18:

AATCCCAAGC CACTGAAG                                                          18

(2) INFORMATION FOR SEQ ID NO: 19:

(i) SEQUENCE CHARACTERISTICS:
             (A) LENGTH: 17 base pairs
             (B) TYPE: nucleotide
             (C) STRANDEDNESS: single strand
             (D) TOPOLOGY: linear (ii) MOLECULE TYPE: other nucleic acid
             (A) DESCRIPTION:   /desc = "oligonucleotide"

(xi) SEQUENCE DESCRIPTION: SEQ ID NO: 19:

CGAGGTCGAC GGTATCG                                                           17

(2) INFORMATION FOR SEQ ID NO: 20:

(i) SEQUENCE CHARACTERISTICS:
             (A) LENGTH: 30 base pairs
             (B) TYPE: nucleotide
             (C) STRANDEDNESS: single strand
             (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 20:

GCAGGTCTCT CAGCTGGGAT GAGGGTGAGG                                              30

(2) INFORMATION FOR SEQ ID NO: 21:

(i) SEQUENCE CHARACTERISTICS:
            (A) LENGTH: 30 base pairs
            (B) TYPE: nucleotide
            (C) STRANDEDNESS: single strand
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 21:

GCAGGTCTCA GCTGAGGAGG AAAACCCCGC                                              30

(2) INFORMATION FOR SEQ ID NO: 22:

(i) SEQUENCE CHARACTERISTICS:
            (A) LENGTH: 27 base pairs
            (B) TYPE: nucleotide
            (C) STRANDEDNESS: single strand
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 22:

GCAGGTCTCT GTTGTGTCGC ACTGGTT                                                 27

(2) INFORMATION FOR SEQ ID NO: 23:

(i) SEQUENCE CHARACTERISTICS:
            (A) LENGTH: 27 base pairs
            (B) TYPE: nucleotide
            (C) STRANDEDNESS: single strand
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 23:

GGTCTCTTTC TTGGCCCGGT TGATCAC                                                 27

(2) INFORMATION FOR SEQ ID NO: 24:

(i) SEQUENCE CHARACTERISTICS:
            (A) LENGTH: 27 base pairs
            (B) TYPE: nucleotide
            (C) STRANDEDNESS: single strand
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 24:

GGTCTCAAGA AAGCAGGGAA GGCCGTC                                                 27

(2) INFORMATION FOR SEQ ID NO: 25:

(i) SEQUENCE CHARACTERISTICS:
            (A) LENGTH: 28 base pairs
            (B) TYPE: nucleotide
            (C) STRANDEDNESS: single strand (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 25:

GGTCTCGTGC ATCAGCAGGC AGGTCGGC                                              28

(2) INFORMATION FOR SEQ ID NO: 26:

(i) SEQUENCE CHARACTERISTICS:
            (A) LENGTH: 29 base pairs
            (B) TYPE: nucleotide
            (C) STRANDEDNESS: single strand
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 26:

GGTCTCATGC ACAGAAGAAT GGCTGCCAG                                             29

(2) INFORMATION FOR SEQ ID NO: 27:

(i) SEQUENCE CHARACTERISTICS:
            (A) LENGTH: 30 base pairs
            (B) TYPE: nucleotide
            (C) STRANDEDNESS: single strand
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 27:

GGTCTCAAAC ATGTACATTC GGCCTCCACC                                            30

(2) INFORMATION FOR SEQ ID NO: 28:

(i) SEQUENCE CHARACTERISTICS:
            (A) LENGTH: 27 base pairs
            (B) TYPE: nucleotide
            (C) STRANDEDNESS: single strand
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 28:

GTCTCCATGT TTCCTGAGGG GACCCCA                                               27

(2) INFORMATION FOR SEQ ID NO: 29:

(i) SEQUENCE CHARACTERISTICS:
            (A) LENGTH: 27 base pairs
            (B) TYPE: nucleotide
            (C) STRANDEDNESS: single strand
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 29:

GGTCTCCTGC CATTCCTGCA CCAGGTT                                               27

(2) INFORMATION FOR SEQ ID NO: 30:

(i) SEQUENCE CHARACTERISTICS:
            (A) LENGTH: 27 base pairs
            (B) TYPE: nucleotide

```
            (C) STRANDEDNESS: single strand
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 30:

GGTCTCTGGC AGGCCAAGCA CCAGGGA                                              27

(2) INFORMATION FOR SEQ ID NO: 31:

(i) SEQUENCE CHARACTERISTICS:
            (A) LENGTH: 27 base pairs
            (B) TYPE: nucleotide
            (C) STRANDEDNESS: single strand
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 31:

GGTCTCCAGG GTCGGGTCCT TGGTGTG                                              27

(2) INFORMATION FOR SEQ ID NO: 32:

(i) SEQUENCE CHARACTERISTICS:
            (A) LENGTH: 25 base pairs
            (B) TYPE: nucleotide
            (C) STRANDEDNESS: single strand
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 32:

GGTCTCGACC CTGGCGGAGA TGACG                                                25

(2) INFORMATION FOR SEQ ID NO: 33:

(i) SEQUENCE CHARACTERISTICS:
            (A) LENGTH: 24 base pairs
            (B) TYPE: nucleotide
            (C) STRANDEDNESS: single strand
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 33:

GGTCTCCTCA GTCAGTGCCA TATA                                                 24

(2) INFORMATION FOR SEQ ID NO: 34:

(i) SEQUENCE CHARACTERISTICS:
            (A) LENGTH: 27 base pairs
            (B) TYPE: nucleotide
            (C) STRANDEDNESS: single strand
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 34:

GGTCTCACTG AGGCGATCAT GTTTGAC                                              27

(2) INFORMATION FOR SEQ ID NO: 35:

(i) SEQUENCE CHARACTERISTICS:
            (A) LENGTH: 23 base pairs
```

(B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 35:

TGCACCAGGT GCGCCTGCGG GCC          23

(2) INFORMATION FOR SEQ ID NO: 36:

(i) SEQUENCE CHARACTERISTICS:
        (A) LENGTH: 27 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 36:

GCCGCACAGC TGGTCTACAA CATGGAT          27

(2) INFORMATION FOR SEQ ID NO: 37:

(i) SEQUENCE CHARACTERISTICS:
        (A) LENGTH: 24 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 37:

GCTGTCTAAG GCCTTGCCGG GGGC          24

(2) INFORMATION FOR SEQ ID NO: 38:

(i) SEQUENCE CHARACTERISTICS:
        (A) LENGTH: 27 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 38:

GCCGCACAGC TGGTCTACAA CATGGAT          27

(2) INFORMATION FOR SEQ ID NO: 39:

(i) SEQUENCE CHARACTERISTICS:
        (A) LENGTH: 25 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 39:

GGGGGTCTCG CTTGCTGCCA TTAAC          25

(2) INFORMATION FOR SEQ ID NO: 40:

(i) SEQUENCE CHARACTERISTICS:

```
        (A) LENGTH: 30 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 40:

GTTAATGGTC TCACAAGCGA GGAACCCTCG                                         30

(2) INFORMATION FOR SEQ ID NO: 41:

(i) SEQUENCE CHARACTERISTICS:
        (A) LENGTH: 27 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 41:

CCCGTGGGTC TCGCTAGCCA GGGGCAC                                            27

(2) INFORMATION FOR SEQ ID NO: 42:

(i) SEQUENCE CHARACTERISTICS:
        (A) LENGTH: 30 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 42:

GTTAATGGTC TCACAAGCGA GGAACCCTCG                                         30

(2) INFORMATION FOR SEQ ID NO: 43:

(i) SEQUENCE CHARACTERISTICS:
        (A) LENGTH: 30 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 43:

GATGCTGGTC TCGGTGGAGG GGGCTGGCAG                                         30

(2) INFORMATION FOR SEQ ID NO: 44:

(i) SEQUENCE CHARACTERISTICS:
        (A) LENGTH: 30 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 44:

CTGCCAGGTC TCACCACCGC CACCAGCATC                                         30

(2) INFORMATION FOR SEQ ID NO: 45:
```

(i) SEQUENCE CHARACTERISTICS:
        (A) LENGTH: 24 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 45:

CATACGATTT AGGTGACACT ATAG                                    24

(2) INFORMATION FOR SEQ ID NO: 46:

(i) SEQUENCE CHARACTERISTICS:
        (A) LENGTH: 27 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 46:

GGTCTCTGGC AGGCCAAGCA CCAGGGA                                 27

(2) INFORMATION FOR SEQ ID NO: 47:

(i) SEQUENCE CHARACTERISTICS:
        (A) LENGTH: 24 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 47:

GTAGAAGCCC CGGGGGTTCC TGCT                                    24

(2) INFORMATION FOR SEQ ID NO: 48:

(i) SEQUENCE CHARACTERISTICS:
        (A) LENGTH: 24 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 48:

AGCAGGAACC CCCGGGGCTT CTAC                                    24

(2) INFORMATION FOR SEQ ID NO: 49:

(i) SEQUENCE CHARACTERISTICS:
        (A) LENGTH: 27 base pairs
        (B) TYPE: nucleotide
        (C) STRANDEDNESS: single strand
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 49:

TGCCATATAA GCTTTGCCGT CATGGTG                                 27

(2) INFORMATION FOR SEQ ID NO: 50:

(i) SEQUENCE CHARACTERISTICS:
        (A) LENGTH: 27 base pairs
        (B) TYPE: nucleotide
        (C) STRANDEDNESS: single strand
        (D) TOPOLOGY: linear (ii) MOLECULE TYPE: other nucleic acid
        (A) DESCRIPTION:  /desc = "oligonucleotide"

(xi) SEQUENCE DESCRIPTION: SEQ ID NO: 50:

GGTCTCTTTC TTGGCCCGGT TCATCAC                                27

(2) INFORMATION FOR SEQ ID NO: 51:

(i) SEQUENCE CHARACTERISTICS:
        (A) LENGTH: 27 base pairs
        (B) TYPE: nucleotide
        (C) STRANDEDNESS: single strand
        (D) TOPOLOGY: linear (ii) MOLECULE TYPE: other nucleic acid
        (A) DESCRIPTION:  /desc = "oligonucleotide"

(xi) SEQUENCE DESCRIPTION: SEQ ID NO: 51:

TGGTCACCAC TCCCACGGAC TTCCCTG                                27

(2) INFORMATION FOR SEQ ID NO: 52:

(i) SEQUENCE CHARACTERISTICS:
        (A) LENGTH: 30 base pairs
        (B) TYPE: nucleotide
        (C) STRANDEDNESS: single strand
        (D) TOPOLOGY: linear (ii) MOLECULE TYPE: other nucleic acid
        (A) DESCRIPTION:  /desc = "oligonucleotide"

(xi) SEQUENCE DESCRIPTION: SEQ ID NO: 52:

GGTCTCAAAC ATGTATTTTC GGCCTCCACC                             30

(2) INFORMATION FOR SEQ ID NO: 53:

(i) SEQUENCE CHARACTERISTICS:
        (A) LENGTH: 30 base pairs
        (B) TYPE: nucleotide
        (C) STRANDEDNESS: single strand
        (D) TOPOLOGY: linear (ii) MOLECULE TYPE: other nucleic acid
        (A) DESCRIPTION:  /desc = "oligonucleotide"

(xi) SEQUENCE DESCRIPTION: SEQ ID NO: 53:

GGTCTCATGT TTCCTGTGGG GACCCCAGAC                             30

(2) INFORMATION FOR SEQ ID NO: 54:

(i) SEQUENCE CHARACTERISTICS:
        (A) LENGTH: 27 base pairs
        (B) TYPE: nucleotide
        (C) STRANDEDNESS: single strand
        (D) TOPOLOGY: linear (ii) MOLECULE TYPE: other nucleic acid
        (A) DESCRIPTION:  /desc = "oligonucleotide"

(xi) SEQUENCE DESCRIPTION: SEQ ID NO: 54:

GGTCTCCTGC CATGCCTGCA CCAGGTT                                27

HIGHLY ACTIVE ALKALINE PHOSPHATASE

The invention concerns a DNA coding a eukaryotic highly active alkaline phosphatase with a specific activity of more than 3000 U/mg. Furthermore the invention concerns a process for the production of the DNA according to the invention as well as a vector containing the DNA according to the invention as well as a cell line containing this vector. The invention additionally concerns a recombinant highly active alkaline phosphatase with a specific activity of more than 3000 U/mg which is coded by the DNA according to the invention.

Alkaline phosphatases (AP) are dimeric, zinc-containing, non-specific phosphomonoesterases which are found in all organisms from E. coli to mammals (McComb et al., 1979). Comparison of the primary structure of different alkaline phosphatases showed a high degree of homology (25–30% homology between E. coli and mammalian AP) (Millán, 1988; Harris, 1989).

In humans and higher animals the AP family consists of four members which are coded on different gene loci (Millán, 1988; Harris, 1989). The alkaline phosphatase family includes the tissue-specific APs (placental AP (PLAP), germ cell AP (GCAP) and intestinal AP (IAP)) and the non-tissue-specific APs (TNAP) which are mainly located in the liver, kidney and bones.

A decisive property of the previously known APs is the large variability of the catalytic activity of the mammalian APs which have a 10–100-fold higher specific activity than E. coli AP. Among the mammalian APs the AP from the bovine intestine (bIAP) exhibits the highest specific activity. This property makes the bIAP attractive for biotechnological applications such as enzyme conjugates for a diagnostic reagent or dephosphorylation of DNA. In 1985 Besman and Coleman proved the existence of two IAP isoenzymes in the bovine intestine, the IAP from the calf intestine and the IAP from the intestine of a mature cow (bIAPs), by amino-terminal sequencing of chromatographically purified AP fractions. A clear difference at the amino terminus was described between the bIAP of the mature cow (LVPVEEED) and the bIAP from calf intestine (LIPAEEEN). In 1993 Weissig et al. achieved an accurate biochemical characterization by cloning a recombinant bIAP (bIAP I) with a specific activity of ca. 3000 U/mg and the N-terminus LVPVEEED. However, bIAPs from calf intestine with specific activities of up to 8000 U/mg are also commercially available (Boehringer Mannheim, Biozyme, Oriental Yeast) which, however, have previously not been further characterized. All attempts at cloning these highly active alkaline phosphatases were unsuccessful. It was therefore not possible to produce a recombinant highly active alkaline phosphatase. However, the possibility of recombinant production is absolutely essential for an economic production of highly active alkaline phosphatase.

Consequently the object of the present invention was to provide highly active alkaline phosphatases by recombinant means which can also be cloned. Highly active within the sense of the present invention means that the alkaline phosphatase according to the invention has an at least 10% increased activity compared to previously known alkaline phosphatases.

The object was achieved according to the invention by the provision of a DNA coding a eukaryotic highly active alkaline phosphatase with a specific activity of more than 3000 U/mg, preferably of at least 3500 U/mg in which the amino acid residue at position 322 is smaller than aspartate. A eukaryotic DNA is preferred within the sense of the present invention. Eukaryotic cDNA is particularly preferred which means a DNA that no longer contains introns. The term "amino acid residue smaller than aspartate" is understood as any amino acid, preferably natural amino acids or amino acids derived therefrom, which has a smaller spatial dimension than the structure of the amino acid aspartate. A DNA according to the invention is preferred in which the amino acid residue 322 is glycine, alanine, threonine, valine or serine. A DNA according to the invention is particularly preferred in which the amino acid residue 322 is glycine or serine. It is quite especially preferred that the amino acid residue 322 is glycine. A DNA according to SEQ ID NO.: 1, 3 and 5 (FIGS. 1,3,5) and the associated amino acid sequence according to SEQ ID NO.: 2, 4 and 6 (FIGS. 2,4,6) are part of the present invention. The present invention also concerns those cDNAs which differ from the aforementioned only in that the N-terminus is longer or shorter in comparison to the cDNAs according to SEQ ID NO.: 2, 4 and 6. In such cases the name for position 322 according to SEQ ID NO.: 2, 4 and 6 changes correspondingly. If for example the N-terminus is x amino acids longer or shorter than SEQ ID NO.: 2, 4 and 6, the relevant position 322 is also shifted by x amino acids. SEQ ID NO.: 1 contains the DNA code for the sequence of the highly active bIAPII isoenzyme. The native enzyme was known but not characterized and not possible to clone. Hence the determination of the amino acid sequence of the highly active bIAP II isoenzyme is a subject matter of the present invention. A highly purified fraction with high specific activity from the calf intestine (Boehringer Mannheim) was used to determine the sequence. Peptide maps of the highly active AP were produced by cleavage with the endoproteinases LysC, AspN, GluC, trypsin and chemical cleavage by bromocyanogen. The peptides produced in this manner were separated and isolated by means of reversed phase HPLC. Each peptide was analysed by electrospray mass spectroscopy and sequenced by means of Edman degradation. The sequences obtained in this way were compared with the published sequence of bIAP I (Weissig et al., 1993). As expected the amino terminus of bIAP II has the start sequence LIPAEEEN as described by Besman and Coleman (J. Biol. Chem. 260, 11190–11193 (1985)). The complete amino acid sequence of bIAP II is shown in SEQ ID NO.: 2 (FIG. 2). According to this the bIAP II has a total of 24 amino acid substitutions compared to bIAP I. The number of amino acids in the isolated highly active bIAP II isoenzyme is 480 amino acids. The nucleotide sequence of 1798 bp (FIG. 1) includes a coding region of 514 amino acids. The amino acids that are possible from position 481 to 514 inclusive can vary within wide limits.

In the following the present invention describes the cloning and complete characterization of two new previously unknown bIAPs (bIAP III and bIAP IV). Northern blot analyses were carried out on RNA samples from different sections of the bovine intestine. A cDNA bank of the probes with the strongest hybridization signal was set up with an oligo dT primer (Stratagene, San Diego, Calif., USA) in the vector IZAP II (Stratagene, San Diego, Calif, USA). The complete bank (1.0×10$^6$ recombinant clones) was screened with the 1075 bp HindIII fragment of bIAP I which covers a region from exon I to VIII of the bIAP I gene. 65 Clones were isolated and sequenced. In this process two new bIAPs were identified (bIAP III and bIAP IV) whose characterization is described further below and were neither completely homologous to bIAP I nor to bIAP II. The nucleotide sequences of bIAP III and IV are shown in FIGS. 3 and 5.

The sequence differences of bIAPs I IV are shown in FIG. 7. However, none of the new bIAPs has the expected N-terminus LIPAEEEN but rather new previously not described N-termini (see FIG. 7). The cDNA of the two new bIAP isoenzymes was recleaved with appropriate restriction enzymes and inserted by ligation into the CHO expression vector pcDNA-3 (e.g. from the Invitrogen Co. San Diego, Calif., USA). The clones which contained the new bIAP isoenzymes were brought to expression according to the method described by Invitrogen and the isoenzymes were characterized. The expression of a bIAP gene in various hosts is described in WO 93/18139 (CHO cells, E. coli, baculovirus system). The methods, vectors and expression systems described in this document are part of the disclosure of the present application. The present invention in addition concerns the native and recombinant highly active alkaline phosphatases bIAP III and bIAP IV. The alkaline phosphatases according to SEQ ID NO.: 4 and 6 are particularly preferred. CHO cell lines containing the bIAP III and bIAP IV gene were deposited at the DSMZ, "Deutsche Sammlung von Mikroorganismen und Zellkulturen GmbH", Mascheroder Weg 1b, D-38124 Braunschweig (DSM ACC 2349, DSM ACC 2350).

In the following the invention describes the construction of the bIAP II sequence by ligation of mutated and wild-type fragments of bIAP I, III and IV. A series of intermediary intermediate products (L1N8, INT 1, INT 2 and INT 3) was generated by this process which code for functional isoenzymes. In order to construct these intermediary intermediate products a section of the bIAP-cDNA to be modified was cleaved out in each case with appropriate restriction enzymes and replaced by a segment of another bIAP-cDNA containing the desired mutations which possesses compatible ends by digestion with restriction enzymes. Mutations which cannot be introduced by ligation of segments of different bIAP-cDNAs were introduced by site-directed mutagenesis. The mutated fragment was subsequently recleaved with appropriate restriction enzymes and ligated into a like-wise cleaved bIAP-cDNA segment with compatible ends (FIG. 8). The mutations introduced in this manner were subsequently checked by restriction analysis and sequencing.

Hence a subject matter of the present invention is a process for the production of the DNA according to the invention characterized in that mutated and wild-type fragments of the DNA of one or several alkaline phosphatases were ligated. Moreover the present invention concerns a cDNA which codes functional isoenzymes and which is formed as intermediate products during the aforementioned process according to the invention. Additionally the present invention concerns a vector containing the cDNA according to the invention.

A further subject matter of the present invention is a cell line containing the vector according to the invention. Suitable cells are for example eukaryotic cells such as CHO, pichia, hansenula or saccharomyces cerevisiae and aspergillus or prokaryotic cells such as E. coli. E. coli, yeast and CHO cells are particularly preferred. Suitable starting vectors for E. coli strains are for example pTE, pTaq, bPL, pBluescript. Suitable E. coli strains are for example XL1-Blue, HB101, RR1 Δ M15, BL21(DE), MC 1000 etc. Suitable pichia vectors are for example pGAPZα and pPICZα (Invitrogen, San Diego, Calif., USA). A suitable vector for CHO cell lines is for example pcDNA-3 (Invitrogen, San Diego, Calif., USA). A CHO cell line containing the bIAP II gene was deposited at the DSMZ, "Deutsche Sammlung von Mikroorganismen und Zellkul-turen GmbH", Mascheroder Weg 1b, D-38124 Braunschweig (DSM ACC 2348).

The kinetic characterization of the recombinant bIAP I, II, III and IV isoenzymes showed considerable differences with regard to the catalytic properties (FIG. 9). For example bIAP II has a more than 300% increased i.e. more than three-fold higher specific activity (ca. 8600 U/mg) than bIAP I (ca. 2700 U/mg). But also bIAP III and bIAP IV exhibit an approximately 1.8-fold (ca. 4700 U/mg) and about 2.6-fold (>6700 U/mg) higher activity respectively than bIAP I (FIG. 9) which corresponds to a percentage increase of ca. 170% and 250% respectively. Furthermore there was a considerable measurable difference in the heat stability of the isoenzymes. bIAP I is the most heat stable isoenzyme, the $T_m$ value of bIAP II and III is 7° C. lower and the $T_m$ value of bIAP IV is 13° C. lower than bIAP I (FIG. 9). The $T_m$ value is understood as the temperature at which a 50% residual activity is measured after an incubation period of 10 minutes.

In the following the invention describes the identification of amino acid residues which influence the specific activity of the bIAPs. This was aided by the intermediary intermediate products. The expression of the intermediary chimers L1N8, INT 1, INT2 and INT3 enabled 11 of the 24 amino acids to be excluded as an effector for the increase in activity (FIG. 7).

The L1N8 mutant enzyme had a comparable specific activity to bIAP I; consequently the mutations V2I, V4A and D8N introduced in this case are not relevant for the increase in the specific activity. The notation V2I means that at position 2 the amino acid valine is replaced by isoleucine.

The INT 1 mutant has a comparable specific activity to bIAP II and consequently this region is important.

The INT 2 mutant has a comparable specific activity to INT 1 and bIAP II and consequently the mutations S380G, D411G, D416E, Q420R, Q427L, E453Q and T480A from INT 2 can also be excluded.

In generating the INT 3 mutants no change in the high specific activity was found thus excluding an effect of the mutation N192Y.

In order to identify which of the 13 remaining residues are crucial for the high specific activity, the bIAP II cDNA was used in the present invention as a template for single mutations against the corresponding amino acid of bIAP I. The single mutants N122K, I133M, A142S, K180M, M205K, E210V, E236A, G322D and I332G as well as a combined A289Q-A294V-Q297R-L299V bIAP II mutant were constructed (FIG. 9).

Surprisingly it was found that mainly the mutation G322D is able to decrease the high specific activity of bIAP II (ca. 8600 U/mg) by more than a factor of 3 (2817 U/mg) and thus to convert it into the comparably low specific activity of bIAP I.

In order to verify this result the reverse mutation D322G was introduced into bIAP I in the present invention. Surprisingly in this case the reverse effect namely an increase of the specific activity of more than 3-fold to 10148 U/mg was measured and hence a comparable value to bIAP II was achieved (FIG. 9). A comparison of the amino acid sequences of the relatively more highly active bIAP III (ca. 4700 U/mg) and the more highly active bIAP IV (>6700 U/mg) again confirm this result. bIAP III has a serine at position in 322 and bIAP IV has a glycine.

In addition in the present invention the generated mutants were in turn examined for heat stability. Consequently the difference in the heat stability between bIAP I and bIAP II is due to a combined effect of more than one substitution. The [G$^{322}$]bIAP I as well as the [D$^{322}$]bIAP II mutants exhibit stability values which lie between those of the bIAP I and bIAP II isoenzymes (FIG. 9). The D322G mutation has a slight destabilizing effect (almost 4° C. in T$_{50}$) on the bIAP I isoenzyme whereas the substitution G322D in bIAP II results in a corresponding increase in the stability of this mutant enzyme. However, the heat stability of the wild-type bIAP I is not achieved.

Hence the subject matter of the present invention is in particular to provide a highly active recombinant alkaline phosphatase with an activity of more than 3000 U/mg which is coded by a eukaryotic cDNA. A highly active recombinant alkaline phosphatase according to the invention is particularly preferred in which a glycine, alanine, threonine, valine or serine is at position 322. An alkaline phosphatase according to the invention is particularly preferred in which a glycine is at position 322.

The highly active recombinant alkaline phosphatase according to the invention can preferably additionally have a mutation at one or several of the following positions:

Amino acid residues at position 1, 108, 125, 149, 181, 188, 219, 221, 222, 223, 224, 231, 252, 258, 260, 282, 304, 321, 330, 331, 354, 383, 385, 400, 405, 413, 428, 431 and 461 in which the mutation causes an increase in activity. Furthermore the present invention concerns a process for the production of the highly active alkaline phosphatase according to the invention. The alkaline phosphatases according to the invention can also be further improved by specific mutagenesis e.g. with regard to their thermostability.

The activity of the highly active alkaline phosphatase according to the invention was determined according to E. Mössner et al., Z. Physiol. Chem. 361 (1980), 543–549; with the difference that the test was carried out at 37° C. rather than at 25° C. as described in the publication. The determination at 37° C. is the world-wide usual temperature at which the activity is measured in diethanol buffer (BM test method 5426).

The protein determination of the APs according to the invention and of the known APs is carried out by measuring the absorbance of the protein solution at 280 nm against water. The absorbance of a low and highly active AP solution at a concentration of 1 mg/ml is 1.0 at 280 nm (A 280 nm (1 mg/ml) equals 1).

The specific activity is determined by forming a quotient of activity relative to the accompanying amount of protein.

FIGURE LEGENDS

FIG. 1:

SEQ ID NO.: 1 nucleotide sequence of bIAP II (1798 bp) Start of the coding region for mature bIAP II at pos. 108, end at pos. 1649

FIG. 2:

SEQ ID NO.: 2 amino acid sequence of bIAP II (480 amino acids) with cleavage sites

FIG. 3:

SEQ ID NO.: 3 nucleotide sequence of bIAP III (2460 bp) Start of the coding region for mature bIAP III at pos. 123, end at pos. 1655

FIG. 4:

SEQ ID NO.: 4 amino acid sequence of bIAP III (511-amino acids)

FIG. 5:

SEQ ID NO.: 5 nucleotide sequence of bIAP IV (2542 bp) Start of the coding region for mature bIAP IV at pos. 122, end at pos. 1654

FIG. 6:

SEQ ID NO.: 6 amino acid sequence of bIAP IV (511 amino acids)

FIG. 7:

Amino acid differences between bIAP I, bIAP II, bIAP III and bIAP IV isoenzymes. Only the residues that are different are shown. The asterisk identifies those positions that were selected for individual mutagenesis in order to identify residues that are responsible for an increased catalytic activity of bIAP II.

FIG. 8:

Ligation strategy for bIAP II DNA

FIG. 9:

Kinetic parameters and heat stability of recombinant wild-type and chimeric bIAP enzymes and mutants of the bIAP enzymes changed by site-directed mutagenesis. *[QVRV]bIAP II is the abbreviation for the [Q$^{289}$, V$^{294}$, R$^{297}$, V$^{299}$]bIAP II mutant.

The invention is further elucidated by the following examples:

Example 1

Cloning

A λgt 11 cDNA bank prepared from the intestine of mature cows (Clontech Laboratories, Palo Alto, Calif., USA) was screened using a 1075 bp Hind III fragment from the 5' end of the bIAP I cDNA as a probe (Weissig et al., 1993). Clones from this cDNA bank were used to screen an EMBL-3 SP6/T7 genomic cDNA bank which was prepared from the liver of mature cows (Clontech Laboratories, Palo Alto, Calif., USA). A non-amplified λZAP II c-DNA bank was set up by means of an oligo dT primer (Stratagene, San Diego, Calif., USA) from mRNA which was isolated from the small intestine of a mature cow using the Trisolv™ reagent and was screened with the 1075 bp HindIII fragment of the bIAP I cDNA as a probe. The probes were radio-labelled using a random primed DNA labeling kit (Boehringer Mannheim). Phage DNA was prepared as described for λgt 11 and EMBL-3 SP6/T7 clones (Tsonis & Manes, 1988). The in vivo cleavage of the λZAP II clones was carried out according to the manufacturer's instructions (Stratagene, San Diego, Calif.). Genomic clones were characterized by Southern blot analysis as described (Sambrook et al., 1989). EcoRI cDNA fragments of λgt 11 clones and different restriction fragments from clones of other banks were subcloned into the KS+vector (Stratagene, San Diego, Calif., USA). Plasmid DNA was prepared by alkaline lysis (Sambrook et al., 1989). The sequencing was carried out using Sequenase according to the manufacturer's protocol (Amersham). The oligo-nucleotides used to sequence the bIAPs III and IV are described in the following: 1s: SEQ ID NO.7: GCC AAG AAT GTC ATC CTC; 1a: SEQ ID NO.8: GAG GAT GAC ATT CTT GGC; 2s: SEQ ID NO.9: GGT GTA AGT GCA GCC GC; 2a: SEQ ID NO.10: GCG GCT GCA CTT AGA CC; 3s: SEQ ID NO. 11: AAT GTA CAT GTT TCC TG; 3a: SEQ ID NO.12: CAG GAA ACA TGT ACA TT; 4s: SEQ ID NO.13: CCA GGG CTT CTA CCT CTT; 4a: SEQ ID NO.14: AAG AGG TAG AAG CCC TGG; 5s: SEQ ID NO.15: ACC AGA GCT ACC ACC TCG; 5a: SEQ ID NO.16: AAG CAG GAA ACC CCA AGA; 6s: SEQ ID NO.17: CTT CAG TGG CTT GGG ATT; 6a: SEQ ID NO.18: AAT CCC AAG CCA CTG AAG. The nucleic acid sequences were analysed with the MacVector sequence analysis program (International Biotechnologies, Inc. New Haven, Conn., USA).

Example 2
Determination of the amino acid sequence of bIAP II

Approximately 500 μg of a purified highly active (ca. 6000 U/mg) bovine intestinal AP was dissolved in 450 μl 6M guanidine hydrochloride, 0.25 M Tris, 1 mM EDTA, pH 8.5 and subsequently 30 μl mercaptoethanol was added. After reduction for 30 minutes at 100° C., the cysteines were alkylated by addition of 35 μl vinylpyridine and this mixture was incubated in the dark for 45 minutes at room temperature. The reaction mixture was then immediately desalted over a short reversed phase HPLC Aquapore RP300 column (30×2.1 mm, Applied Biosystems, Weiterstadt). A step gradient of acetonitrile in 0.1% trifluoroacetic acid was used to elute bound enzymes. Fractions containing protein were evaporated to dryness. In order to deglycosylate the enzyme 125 μg AP was dissolved in 15 μl distilled water and 6 μl incubation buffer (250 mM Na$_2$HPO$_4$, 50 mM EDTA, pH 7.2) and 15 U EndoF/PNGase (Boehringer Mannheim, Penzberg). The mixture was kept overnight at 37° C. and subsequently used for cleavage. Reduced and alkylated AP was enzymatically cleaved with various enzymes according to the instructions on the data sheets of the individual enzymes (endoproteinase LysC, endoproteinase AspN, endoproteinase GluC and trypsin (Boehringer Mannheim, Penzberg). Cyanogen bromide cleavage was carried out for 8 hours using 10% (w/w) CNBr in 70% (v/v) formic-acid. After dissolving with water, the volume of the solution was reduced using a SpeedVac concentrator (Savant) and used for a reversed phase HPLC. The C-terminal tryptic peptide was digested for 4 minutes with carboxypeptidase Y (8 ng/μl) and the released peptides were analysed according to the manufacturer's instructions with matrix-supported laser desorption/ionisation mass spectrometry using a Bruker Reflex III instrument. 2,5 Dihydroxybenzoic acid (10 mg/ml) in acetonitrile/water (50/50, v/v) was used as the matrix. Peptides from enzymatic or chemical cleavages were separated by reversed phase HPLC on a LiChrospher C18 selB column 125×2 mm (Merck, Darmstadt) using a 0.1% trifluoroacetic acid/acetonitrile solvent system. The flow rate was 300 μl/min. The eluant was detected by UV monitoring at 206 nm and the fractions were collected manually. The mass determination of the peptides was carried out with an API III electrospray mass spectrometer (PE-Sciex, Langen) according to the manufacturer's instructions. The amino acid sequence was determined with a 492 A protein sequencer (Applied Biosystems, Weiterstadt) according to the manufacturer's instructions.

Example 3
Preparation of the bIAP II cDNA and bIAP II mutagenesis

In order to prepare a cDNA which codes for bIAP II, wild-type restriction fragments and site-directed mutagenized PCR fragments of the cDNAs bIAP I, III and IV were ligated with one another and the L1N8 (3 fragments) and INT 1 (9 fragments) cDNA intermediate constructs were created. INT 1 and bIAP III then served as a template for the site-directed mutagenesis and fragments from this were assembled to form the complete INT 2 (8 fragments) cDNA. Restriction fragments of INT 2 and site-directed mutagenized fragments of INT 2 were then assembled to form the INT 3 (5 fragments) cDNA and finally to form the bIAP II (4 fragments) cDNA. The site-directed mutagenesis was carried out according to the method of Tomic et al. (1990) using Bsa I (type II s) as the restriction enzyme which cleaves at a distance from its recognition sequence (GGTCTCN1/N5). All PCR products were sequenced in order to verify the absence of secondary mutations. All constructs were confirmed by sequencing and restriction digestion. The sequence of the oligonucleotide primers used to amplify the site-directed mutagenized fragments are as follows: the name of the primer is mentioned first followed by the sequence (positions that indicate the mutations are underlined: KS:SEQ ID NO.19: CGA GGT CGA CGG TAT CG; 1L:SEQ ID NO.20: GCA GGT CTC TCA GCT GGG ATG AGG GTG AGG; 8N:SEQ ID NO.21: GCA GGT CTC AGC TGA GGA GGA AAA CCC CGC; 122:SEQ ID NO.22: GCA GGT CTC TGT TGT GTC GCA CTG GTT; 1s:SEQ ID NO.7: GCC AAG AAT GTC ATC CTC; M133I:SEQ ID NO.23: GGT CTC TTT CTT GGC CCG GTT GAT CAC; S142A:SEQ ID NO.24: GGT CTC AAG AAA GCA GGG AAG GCC GTC; 180:SEQ ID NO.25: GGT CTC GTG CAT CAG CAG GCA GGT CGG C; M180K:SEQ ID NO.26: GGT CTC ATG CAC AGA AGA ATG GCT GCC AG; K205M:SEQ ID NO.27: GGT CTC AAA CAT GTA CAT TCG GCC TCC ACC; V210E:SEQ ID NO.28: GT CTC CAT GTT TCC TGA GGG GAC CCC A; A236E:SEQ ID NO.29: GGT CTC CTG CCA TTCCTG CAC CAG GTT; 236:SEQ ID NO.30: GGT CTC TGG CAG GCC AAG CAC CAG GGA; 289:SEQ ID NO.31: GGT CTC CAG GGT CGG GTC CTT GGT GTG; E289A:SEQ ID NO.32: GGT CTC GAC CCT GGC GGA GAT GAC G; 330:SEQ ID NO.33: GGT CTC CTC AGT CAG TGC CAT ATA; 330E,V332I:SEQ ID NO.34: GGT CTC ACT GAG GCG ATC ATG TTT GAC; XIa:SEQ ID NO.35: TG CAC CAG GTG CGC CTG CGG GCC; N192Y:SEQ ID NO.36: GCC GCA CAG CTG GTC TAC AAC ATG GAT; S380G:SEQ ID NO.37: GCT GTC TAA GGC CTT GCC GGG GGC; N192Y:SEQ ID NO.38: GCC GCA CAG CTG GTC TAC AAC ATG GAT; D411G:SEQ ID NO.39: GGG GGT CTC GCT TGC TGC CAT TAA C: D416E:SEQ ID NO.40: GTT AAT GGT CTC ACA AGC GAG GAA CCC TCG; S428A:SEQ ID NO.41: CCC GTG GGT CTC GCT AGC C CAG GGG CAC; D416E:SEQ ID NO.42: GTT AAT GGT CTC ACA AGC GAG GAA CCC TCG; T480S:SEQ ID NO.43: GAT GCT GGT CTC GGT GGA GGG GGC TGG CAG; 480:SEQ ID NO.44: CTG CCA GGT CTC ACC ACC GCC ACC AGC ATC; SP6:SEQ ID NO.45: CAT ACG ATT TAG GTG ACA CTA TAG; 236:SEQ ID NO.46: GGT CTC TGG CAG GCC AAG CAC CAG GGA; Q304R-:SEQ ID NO.47: GTA GAA GCC CC G GGG GTT CCT GCT; Q304+:SEQ ID NO.48:AGC AGG AAC CCC CGG GGC TTC TAC; E321D:SEQ ID NO.49: TGC CAT ATA AGC TTT GCC GTC ATG GTG. The various PCR reactions are numbered 1–16, the templates are either wild-type cDNAs bIAP I, III or IV or the chimeric constructs INT 1 or INT 2. The oligonucleotide primers (1L in parantheses) are stated above. 1. bIAP IV (KS, 1L); 2. bIAP IV (8N, 122); 3. bIAP III (1S, M133I); 4.bIAP I (S142A, 180); 5. bIAP I (M180K, K205M); 6. bIAP I(V210E, A236E); 7. bIAP I (236, 289); 8. bIAP IV (E289A, 330); 9. bIAP III (330E, V332I, XIa); 10. INT1 (N192Y, S380G); 11. INT1 (N192Y, D411G); 12. bIAP III (D416E, S428A); 13. INT1 (D416E, T480S); 14. INT1 (480, SP6); 15. INT2 (236, Q304R–); 16. INT2 (Q304R+, E321D). The following ligation reactions were carried out in all cases using the pcDNA-3 (Invitrogen, San Diego, Calif.) expression vector. The fragments are numbered according to the aforementioned PCR reaction numbers or named with the name of the wild-type or the chimeric cDNA followed by the restriction enzymes which were used to form the cohesive terminus of this fragment. L1N8 =pcDNA-3/EcoRI-XbaI+ 1/EcoRI-BsaI+2/BsaI-BamHI+bIAP I/BamHI-XbaI. INT 1=pcDNA-3/EcoRI-XbaI+L1N8/EcoRI-NcoI+3/NcoI-BsaI+4/BsaI+5/BsaI+6/BsaI+7/BsaI+8/BsaI+9/BsaI-StuI+ bIAP I/StuI-XbaI. INT 2 =pcDNA- 3/EcoRI-NotI+INT1/ EcoRI-PstI+10/PstI-StuI+11/StuI-BsaI+12/BsaI+13/BsaI+ 14/BsaI+bIAP I/BsaI-NotI. INT 3 =pcDNA-3/EcoRI-XbaI+ INT2/EcoRI-NcoI+INT2/NcoI-PvuII+10/PvuII-EagI+ INT2/EagI-HindIII+INT2/HindIII-XbaI. bIAP II=pcDNA- 3/EcoRI-XbaI+INT3/EcoRI-EagI+15/EagI-SmaI+16/SmaI-HindIII+INT3/HindIII-XbaI.

10 Additional constructs were prepared in order to identify the residue (the residues) which are responsible for the various kinetic properties of bIAP I and II. All constructs were subcloned in pcDNA-3/EcoRI-XbaI. 5 Constructs were prepared by exchange of restriction fragments between L1N8 or bIAP I (I) and bIAP II (II). L1N8 EcoRI-Pm1I and (II) Pm1I-XbaI were ligated in order to prepare the [N122K] bIAP II mutant cDNA. (II) EcoRI-BstEII, (I) BstEII-PvuII, (II) PvuII XbaI were combined for the [K180M]bIAP II mutant cDNA. (II) EcoRI-EagI, (I) EagI-BstEII, (II) BstEII-XbaI were ligated for the [A289Q, A294V, Q297R, L299V] bIAP II mutant. (II) EcoRI-EagI, (II) EagI-BstEII, (I) BstEII-HindIII, (II) HindIII-XbaI for the [G322D]bIAP II mutant. (II) EcoRI-HindIII, (I) HindIII-SacI, (II) SacI-XbaI for the [I332G]bIAP II mutant. 5 other positions required new site-directed mutagenesis. The following oligonucleotides were used for this: I133M-:SEQ ID NO.50: GGT CTC TTT CTT GGC CCG GTT CAT CAC; A142S-:SEQ ID NO.51: TGG TCA CCA CTC CCA CGG ACT TCC CTG; M205K-:SEQ ID NO.52: GGT CTC AAA CAT GTA TTT TCG GCC TCC ACC; E210V+:SEQ ID NO.53: GGT CTC ATG TTT CCT GTG GGG ACC CCA GAC; E236A:SEQ ID NO.54: GGT CTC CTG CCA TGC CTG CAC CAG GTT. The following 8 PCR reactions (a–h) with bIAP II as the template were carried out using these and the previously listed oligonucleotides: a. 1s, I133M-; b. S142A+, M205K-; c. 1s, A142S-; d. V210E+, 330-; e. E210V+, 330-; f. M180K+, E236A-; g. 236+, 330-; h. S142A, K205M-. The products which were formed from this were subcloned and sequenced and then the fragments were isolated for the following ligations: (II) EcoRI-NcoI, (a) NcoI-BsaI, (b) BsaI, PvuII, (II) PvuII-XbaI for I133M. (II) EcoRI-NcoI, (c) NcoI-BstEII, (II) BstEII-PvuII, (II) PvuII-XbaI for A142S. (II) EcoRI-BstEII, (b) BstEII-BsaI, (d) BsaI-HindIII, (II) HindIII-XbaI for M205K. (II) EcoRI-BstEII, (h) BstEII-BsaI, (e) BsaI-HindIII, (II) HindIII-XbaI for E210V. (II) EcoRI-NcoI, (II) NcoI-PvuII, (f) PvuII-BsaI, (g) BsaI-HindIII, (II) HindIII-XbaI for E236A.

Example 4
Production and characterization of recombinant enzymes

All cDNAs (bIAP I, bIAP II, bIAP III, bIAP IV and corresponding mutants) were cloned into the pcDNA-3 expression vector (Invitrogen, San Diego, Calif., USA), transferred into ovarial cells of a chinese hamster (CHO cells) and stable transfectants were selected by growing the cells in the presence of 500 µg/ml geneticin (Gibco, BRL). Recombinant APs were extracted as described from stably transferred CHO cells (Hoylaerts et al., 1997). Microtitre plates that were coated with 0.1 µg/ml high affinity antibovine AP monoclonal antibody (Scottish Antibody Production Unit, Lanarkshire, Scotland) were incubated with increasing enzyme concentrations in order to measure the $k_{cat}$. The activity of the bound enzyme was measured as the change in absorbance with time at 405 nm and 20° C. after addition of 30 mM p-nitrophenyl phosphate (pNPP) as the substrate in 1.0 M diethanolamine buffer (pH 9.8), 1 mM $MgCl_2$ and 20 µM $ZnCl_2$. The concentration of the p-nitrophenol that formed was calculated with an extinction coefficient of 10,080 litre $mole^{-1}$ $cm^{-1}$. Commercial preparations with known specific activities (Biozyme Laboratories, 7822 U/mg and Boehringer Mannheim, 3073 U/mg) and also purified bIAP II (8600 U/mg) were used as standards. The enzyme concentration in these solutions which saturated the antibody (E°) was calculated from a standard curve of activity against known enzyme concentrations under identical test conditions. The maximum substrate conversion ($V_{max}$) was then divided by E° in order to calculate $k_{cat}$. In order to calculate $K_m$ the substrate concentration was changed between 0.25–2.0 mM p-nitrophenyl phosphate (pNPP) and the initial reaction rate at 20° C. was measured over a period of 10 minutes. Regression curves of [pNPP]/v versus [pNPP] (Hanes curves) as the X axis yielded $-K_m$. Division of the standard deviation of the calculated y value for each x value in the regression by the slope of regression yielded the standard deviation of $K_m$. $V_{max}$±standard deviation was calculated using the appropriate equations by dividing $K_m$± standard deviation by the y intercept±standard deviation. The specific activities were calculated in comparison to Biozyme on the basis of antibody-saturated activity. Heat stability curves were established by incubation of extracts at 45–75° C. with an increase in 5° C. steps every 10 minutes as described previously (Weissig et al., 1993). The activity of each sample was then determined as described above and the residual activity was calculated as the residual percentage compared to the non-heated sample. The temperature at which 50% residual activity remains ($T_{50}$) was calculated from the residual activity against temperature curves.

What is claimed is:

1. A highly active recombinant alkaline phosphatase with a specific activity of more than 3000 U/mg which is coded by a DNA in which the triplet which codes for the amino acid residue corresponding to the amino acid residue at position 322 of SEQ ID NO 2, 4 or 6 codes for an amino acid residue that is smaller than aspartate.

2. The alkaline phosphatase of claim 1, wherein said amino acid residue 322 is selected from the group consisting of glycine, alanine, threonine, valine and serine.

3. The alkaline phosphatase of claim 1, wherein said amino acid residue 322 is selected from the group consisting of glycine and serine.

4. The alkaline phosphatase of claim 1, wherein said amino acid residue 322 is glycine.

5. The alkaline phosphatase of claim 1, wherein said DNA has a nucleotide sequence as shown in FIG. 1 (SEQ ID NO.: 1).

6. The alkaline phosphatase of claim 1, wherein said DNA has a nucleotide sequence as shown in FIG. 3 (SEQ ID NO.: 3).

7. The alkaline phosphatase of claim 1, wherein said DNA has a nucleotide sequence as shown in FIG. 5 (SEQ ID NO.: 5).

8. The highly active recombinant alkaline phosphatase of claim 1, wherein said DNA has an additional mutation at an amino acid position selected from the group consisting of 1, 108, 125, 149, 181, 188, 219, 221, 222, 223, 224, 231, 252, 258, 260, 282, 304, 321, 330, 331, 354, 383, 385, 400, 405, 413, 428, 431 and 461.

9. An isolated highly active alkaline phosphatase comprising the amino acid sequence shown in SEQ ID NO.: 4.

10. An isolated highly active alkaline phosphatase comprising the amino acid sequence shown in SEQ ID NO.: 6.

* * * * *